US012285217B2

(12) United States Patent
Kamthan et al.

(10) Patent No.: US 12,285,217 B2
(45) Date of Patent: Apr. 29, 2025

(54) METHODS, DEVICES, AND SYSTEMS FOR MONITORING INTRAOCULAR PRESSURE

(71) Applicant: Icahn School of Medicine at Mount Sinai, New York, NY (US)

(72) Inventors: Gautam Kamthan, New York, NY (US); Tsontcho Ianchulev, Harrison, NY (US)

(73) Assignee: ICAHN SCHOOL OF MEDICINE AT MOUNT SINAI, New York, NY (US)

( * ) Notice: Subject to any disclaimer, the term of this patent is extended or adjusted under 35 U.S.C. 154(b) by 0 days.

(21) Appl. No.: 17/320,736

(22) Filed: May 14, 2021

(65) Prior Publication Data

US 2021/0353145 A1  Nov. 18, 2021

Related U.S. Application Data

(60) Provisional application No. 63/025,617, filed on May 15, 2020.

(51) Int. Cl.
 *A61B 3/16* (2006.01)
 *A61B 5/03* (2006.01)
(52) U.S. Cl.
 CPC ............... *A61B 3/16* (2013.01); *A61B 5/03* (2013.01); *A61B 2562/0247* (2013.01)
(58) Field of Classification Search
 CPC ..... A61B 3/16; A61B 5/03; A61B 2562/0247; A61M 2210/0612; A61M 2205/3344; A61F 9/00736; A61F 9/00781
 See application file for complete search history.

(56) References Cited

U.S. PATENT DOCUMENTS

| | | | |
|---|---|---|---|
| 7,192,412 B1 * | 3/2007 | Zhou | A61F 9/00781 604/8 |
| 8,430,840 B2 | 4/2013 | Nazarifar et al. | |
| 9,295,582 B2 * | 3/2016 | Rockley | A61F 9/00736 |
| 9,566,188 B2 | 2/2017 | Raney et al. | |
| 10,137,034 B2 | 11/2018 | Heeren | |
| 2006/0052666 A1 | 3/2006 | Kumar et al. | |

(Continued)

FOREIGN PATENT DOCUMENTS

| | | |
|---|---|---|
| WO | WO-2019094004 A1 | 5/2019 |
| WO | WO-2021231853 A1 | 11/2021 |

OTHER PUBLICATIONS

Lee, Jeong Oen et al., A microscale optical implant for continuous in vivo monitoring of intraocular pressure, 2017, Microsystems & Nanoengineering 3, 17057; doi:10.1038/micronano.2017.57.

(Continued)

*Primary Examiner* — Devin B Henson
(74) *Attorney, Agent, or Firm* — Wilson Sonsini Goodrich & Rosati

(57) ABSTRACT

Disclosed herein are methods, devices, and systems for monitoring fluid outflow behavior of an eye of a subject, for example, during ocular surgery. Changes to intraocular pressure can reflect fluid outflow behavior. Fluid outflow behavior can be a critical factor in the successful outcome of a surgery and determining likelihood of post-operative side effects. Large fluctuations in intraocular pressure, ocular hypertension, and hypotony can be associated with vision loss or poor ocular health.

40 Claims, 12 Drawing Sheets

System 200

(56) References Cited

U.S. PATENT DOCUMENTS

| | | | |
|---|---|---|---|
| 2011/0015512 A1* | 1/2011 | Pan | A61B 3/16 600/399 |
| 2014/0275923 A1* | 9/2014 | Haffner | A61B 3/16 600/377 |
| 2015/0085249 A1 | 3/2015 | Abreu | |
| 2019/0099546 A1* | 4/2019 | Keh | A61M 3/0216 |

OTHER PUBLICATIONS

Sherwood, Joseph M. et al., Measurement of Outflow Facility Using iPerfusion, Mar. 7, 2016, PLoS ONE11(3): e0150694. doi:10.1371/journal.pone.0150694, pp. 1-29.

International Search Report dated Aug. 31, 2021 for International Application Serial No. PCT/US21/32436 (9 pages).

Karyotakis, N. et al., "Manometric measurement of the outflow facility in the living human eye and its dependence on intraocular pressure", Acta Ophthalmologica, 2015, vol. 93, pp. e343-e348.

International Preliminary Report on Patentability dated Nov. 15, 2022 for International Application Serial No. PCT/US2021/032436, (7 pages).

* cited by examiner

METHODS, DEVICES, AND SYSTEMS FOR MONITORING INTRAOCULAR PRESSURE

CROSS-REFERENCE

This patent application claims the benefit of U.S. Provisional Patent Application No. 63/025,617 filed May 15, 2020, the contents of which are incorporated herein by reference.

BACKGROUND

Intraocular pressure (IOP) is a critical factor in the success of a surgery and determining likelihood of post-operative side effects. Changes in IOP can be used to infer changes in fluid outflow behavior of the eye. Large fluctuations in IOP, ocular hypertension, and hypotony can be associated with vision loss or poor ocular health.

SUMMARY

The present disclosure is related to medical diagnostic systems, devices, and methods, particularly for measuring intraocular fluid outflow and fluid balance in an organ such as the eye and monitoring behavior of the organ based on the measured pressure biometry. Systems, devices, and methods are provided for monitoring fluid outflow behavior of an eye based on continuous measurements of intraocular pressure, including when the eye is left alone, before, during, and after a surgical procedure, and also in response to fluid infusion. Changes to intraocular pressure can reflect the behavior of fluid outflow of the eye, such as naturally through the trabecular meshwork of the eye as well as through an artificial leakage. Fluid outflow behavior can be a critical factor in the successful outcome of a surgery and determining likelihood of post-operative side effects. Large fluctuations in intraocular pressure, ocular hypertension, and hypotony can be associated with vision loss or poor ocular health. Based on real-time intraoperative fluid biometry, pressure dynamics, or post-infusion intraocular pressure response and fluid outflow behavior, methods described herein can help guide medical intervention, reduce the incidence of post-operative ocular pressure spikes or depressions, as well as improve the efficacy of intraocular pressure modifying procedures. Using the systems and devices described herein, a health practitioner can more accurately gauge the fluidic state of an eye before, during, and after surgery. The health practitioner can adjust a medical procedure accordingly, making the procedure more controlled and patient-specific and leading to improved outcomes.

In some embodiments, the invention provides a system for monitoring a fluid outflow behavior of an eye of a subject, comprising: an infusion line configured to be inserted into the eye of the subject; a sensor communicatively coupled to the infusion line, wherein the sensor is configured to continuously detect an intraocular pressure of the eye over a time period; and a processor communicatively coupled to the infusion line and the sensor, wherein the processor is configured to generate a representation of the fluid outflow behavior of the eye based on the intraocular pressure of the eye over the time period. In some cases, the representation of the fluid outflow behavior is visual, audio, or tactile. In some cases, the infusion line provides fluid communication between a fluid source and the eye of the subject. In some cases, the infusion line is configured to be inserted into the eye of the subject through a probe. In some cases, the sensor is communicatively coupled to the infusion line at the probe. In some cases, the sensor is communicatively coupled to the infusion line remotely from the probe. In some cases, the probe comprises a transcorneoscleral port. In some cases, the sensor is configured to continuously detect the intraocular pressure of the eye in real-time. In some cases, the sensor is configured to continuously detect the intraocular pressure of the eye in vivo. In some cases, the processor is configured to generate the representation of the fluid outflow behavior of the eye concurrently with the detecting of the intraocular pressure of the eye by the sensor. In some cases, the system further comprises a pump communicatively coupled to the infusion line, wherein the pump is configured to infuse a replacement fluid into the eye of the subject through the infusion line, and wherein the representation of the fluid outflow behavior of the eye is further based on a change to the intraocular pressure of the eye in response to an infusion of the replacement fluid into the eye.

In some embodiments, the invention provides a method of monitoring a fluid outflow behavior of an eye of a subject, comprising: inserting an infusion line into the eye of the subject; continuously detecting an intraocular pressure of the eye over a time period; and performing an intervention on the eye of the subject based on the intraocular pressure of the eye detected over the time period. In some cases, the infusion line provides fluid communication between a fluid source and the eye of the subject. In some cases, the inserting of the infusion line into the eye of the subject is through a probe. In some cases, the detecting of the intraocular pressure of the eye is in real-time. In some cases, the detecting of the intraocular pressure of the eye is in vivo. In some cases, the detecting of the intraocular pressure of the eye of the subject is while the subject is undergoing a surgery. In some cases, the intervention modulates the fluid outflow behavior of the eye of the subject. In some cases, the method further comprises modifying the intervention on the eye of the subject based on the intraocular pressure of the eye detected over the time period. In some cases, the method further comprises infusing a replacement fluid into the eye of the subject through the infusion line. In some cases, the method further comprises, after infusing the replacement fluid into the eye, continuously detecting the intraocular pressure of the eye over a later time period. In some cases, the time period is a duration of a surgical procedure being performed on the eye of the subject. In some cases, the time period is at least 3 seconds. In some cases, the intraocular pressure of the eye is detected by a sensor that is in fluid communication with the infusion line.

In some embodiments, the invention provides a method of monitoring a fluid outflow behavior of an eye of a subject, comprising: continuously detecting an intraocular pressure of the eye over a time period; monitoring the fluid outflow behavior of the eye of the subject based on the intraocular pressure of the eye detected by the sensor over the time period; and generating a representation of the fluid outflow behavior of the eye. In some cases, the detecting of the intraocular pressure of the eye is in real-time. In some cases, the detecting of the intraocular pressure of the eye is in vivo. In some cases, the detecting of the intraocular pressure of the eye of the subject is while the subject is undergoing a surgery. In some cases, the generating of the graphical representation of the fluid outflow behavior of the eye is concurrent with the detecting of the intraocular pressure of the eye. In some cases, the method further comprises infusing a replacement fluid into the eye of the subject through an infusion line. In some cases, the infusion line provides fluid communication between a fluid source and the eye of the subject. In some cases, the method further comprises, after infusing the replacement fluid into the eye, continuously detecting the intraocular pressure of the eye over a later time period. In some cases, the intraocular pressure of the eye is detected from a sensor that is in fluid communication with the infusion line. In some cases, the time period is at least 3 seconds. In some cases, the intraocular pressure of the eye is detected by a sensor that is in fluid communication with the infusion line. In some cases, the representation of the fluid outflow behavior is visual, audio, or tactile.

In some embodiments, the invention provides a system for monitoring a fluid outflow behavior of a tissue compartment of a subject, comprising: an infusion line configured to provide fluid communication between a fluid source and the tissue compartment of the subject; a sensor configured to detect a pressure within the tissue compartment over a time period; and a processor configured to generate a representation of the pressure within the tissue compartment over the time period. In some cases, a change in the pressure within the tissue compartment over the time period corresponds to the fluid outflow behavior of the tissue compartment. In some cases, the sensor is configured to continuously detect the pressure within the tissue compartment. In some cases, the sensor is configured to continuously detect the pressure within the tissue compartment in real-time. In some cases, the processor is configured to continuously generate the graphical representation of the pressure within the tissue compartment. In some cases, the processor is configured to continuously generate the representation of the pressure within the tissue compartment in real-time. In some cases, the display is configured to electronically display a visual representation of the pressure within the tissue compartment. In some cases, the representation of the fluid outflow behavior is visual, audio, and/or tactile. In some cases, the display is communicatively coupled to the processor. In some cases, the system further comprises a pump configured to infuse a replacement fluid from the fluid source to the tissue compartment of the subject. In some cases, the system further comprises a probe configured to be inserted into the tissue compartment of the subject. In some cases, the infusion line is configured to provide fluid communication between the fluid source and the tissue compartment of the subject through the probe. In some cases, the time period is a duration of a surgical procedure performed on the subject. In some cases, the time period is any detection period desired by a user of the device.

In some embodiments, the invention provides a system for monitoring a fluid outflow behavior of an eye of a subject, comprising: an infusion line configured to provide fluid communication between a fluid source and the eye of the subject; a sensor configured to detect an intraocular pressure of the eye over a time period; and a processor configured to generate a representation of the intraocular pressure of the eye over the time period. In some cases, a change in the intraocular pressure of the eye over the time period corresponds to the fluid outflow behavior of the eye. In some cases, the sensor is configured to continuously detect the intraocular pressure of the eye. In some cases, the sensor is configured to continuously detect the intraocular pressure of the eye in real-time. In some cases, the processor is configured to continuously generate the representation of the intraocular pressure of the eye. In some cases, the processor is configured to continuously generate the representation of the intraocular pressure of the eye in real-time. In some cases, the display is configured to electronically display a representation of the intraocular pressure of the eye. In some cases, the display is communicatively coupled to the processor. In some cases, the system further comprises a pump configured to infuse a replacement fluid from the fluid source to the eye of the subject. In some cases, the replacement fluid is a saline solution or a pH balanced solution. In some cases, the system further comprises a probe configured to be inserted into the eye of the subject. In some cases, the infusion line is configured to provide fluid communication between the fluid source and the eye of the subject through the probe. In some cases, the time period is a duration of a surgical procedure performed on the subject. In some cases, the time period is any detection period desired by a user of the device. In some cases, the representation of the intraocular pressure of the eye is visual, audio, or tactile.

In some embodiments, the invention provides a method comprising: inserting an infusion line into the eye of the subject, wherein the infusion line provides fluid communication between a fluid source and the eye of the subject; detecting an intraocular pressure of the eye over a time period; monitoring the fluid outflow behavior of the eye of the subject based on the intraocular pressure of the eye detected by the sensor over the time period; and performing an intervention on the eye of the subject based on fluid outflow behavior of the eye. In some cases, a change in an intraocular pressure of the eye over the time period corresponds to the fluid outflow behavior of the eye. In some cases, the infusion line is inserted into the eye of the subject through a probe. In some cases, the detecting of the intraocular pressure of the eye is continuous. In some cases, the detecting of the intraocular pressure of the eye is in real-time. In some cases, the detecting of the intraocular pressure of the eye is while the subject is undergoing a medical procedure, e.g., a surgery. In some cases, the intervention is a surgical procedure, modification of a procedure, abortion of a procedure, or a pharmaceutical intervention. In some cases, the intervention modulates the fluid outflow behavior of the eye of the subject. In some cases, the intervention modulates the intraocular pressure of the subject. In some cases, the method further comprises making an incision in the eye of the subject. In some cases, the method further comprises analyzing an electronical display of the representation of the fluid outflow behavior of the eye. In some cases, the representation of the fluid outflow behavior of the eye is visual, audio, and/or tactile. In some cases, the method further comprises inferring a prognosis of the subject based on the fluid outflow behavior of the eye. In some cases, the method further comprises infusing a volume of a replacement fluid into the eye of the subject from a fluid source through the infusion line. In some cases, the replacement fluid is a saline solution or a pH balanced solution.

In some embodiments, the invention provides a method of monitoring a fluid outflow behavior of an eye of a subject, comprising: detecting an intraocular pressure of the eye over a time period, wherein the infusion line provides fluid communication between a fluid source and the eye of the subject; monitoring the fluid outflow behavior of the eye of the subject based on the intraocular pressure of the eye detected by the sensor over the time period; and generating a representation of the fluid outflow from behavior of the eye. In some cases, a change in an intraocular pressure of the eye over the time period corresponds to the fluid outflow behavior of the eye. In some cases, the detecting of the intraocular pressure is continuous. In some cases, the detecting of the intraocular pressure is in real-time. In some cases, the detecting of the intraocular pressure is while the subject is undergoing a medical procedure. In some cases, the method further comprises actuating infusion of a volume of a replacement fluid to the eye of the subject through the infusion line. In some cases, the replacement fluid is a saline solution or a pH balanced solution. In some cases, the generating of the representation of the fluid outflow behavior of the eye is by a processor. In some cases, the representation of the fluid outflow behavior of the eye is visual, audio, and/or tactile. In some cases, the generating of the representation of the fluid outflow behavior is continuous. In some cases, the generating of the representation of the fluid outflow behavior of the eye is in real-time. In some cases, the generating of the representation of the fluid outflow behavior is concurrent with detection of the intraocular pressure of the eye over the time period. In some cases, the method further comprises receiving data associated with the intraocular pressure of the eye over the time period. In some cases, the method further comprises transmitting data associated with the intraocular pressure of the eye over the time period. In some cases, the method further comprises electronically displaying the representation of the fluid outflow behavior of the eye. In some cases, the method further comprises recommending an intervention for the subject based on the fluid outflow behavior of the eye. In some cases, the method further comprises performing an intervention on the eye based on the fluid outflow behavior of the eye. In some cases, the intervention modulates the fluid outflow behavior of the eye. In some cases, the method further comprises modifying a surgical procedure to be performed on the subject based on the fluid outflow behavior of the eye. In some cases, the method further comprises determining a prognosis of the subject based on the fluid outflow behavior of the eye.

INCORPORATION BY REFERENCE

Each patent, publication, and non-patent literature cited in the application is hereby incorporated by reference in its entirety as if each was incorporated by reference individually.

DETAILED DESCRIPTION

Figure 1:
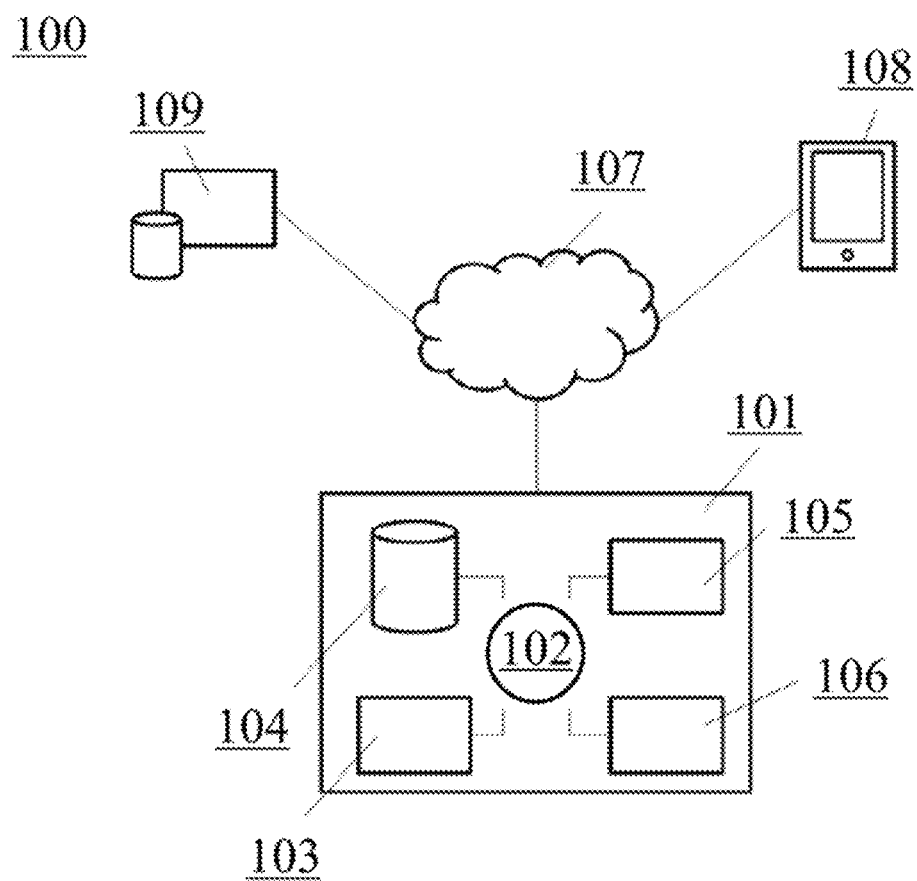
FIG. 1 illustrates an example computer system of the invention.

Described herein are methods, devices, and systems for monitoring dynamic changes in fluid outflow from a tissue compartment of a subject. The methods, devices, and systems can continuously monitor pressure changes associated with the dynamic changes in fluid outflow from a tissue compartment. A system can include an infusion line configured to provide fluid communication between a fluid source and the tissue compartment of the subject; a sensor configured to detect a pressure within the tissue compartment over a time period; and a processor configured to generate a representation of the fluid outflow behavior of the tissue compartment based on the pressure within the tissue compartment detected by the sensor over the time period. The tissue compartment can be an ocular tissue compartment, an endothelial tissue compartment, a cardiac tissue compartment, pulmonary tissue compartment, or any tissue compartment in a body of a subject that is suitable for characterizing fluid homeostasis and/or determining pressure fluctuations based on fluid outflow behavior. The representation of the fluid outflow behavior can be visual, audio, and/or tactile.

Further described herein are methods, devices, and systems for monitoring dynamic changes in fluid outflow from a tissue compartment of a subject during a medical procedure being performed on the subject and modifying the medical procedure based on the observed changes in fluid outflow from a tissue compartment of the subject. The modification can modulate a change in fluid outflow from a tissue compartment of the subject. The medical procedure can be performed on a body part or tissue compartment of a subject, including, but not limited to, the eye, the heart, the skull, the abdomen, the chest, and blood vessels. Systems and devices described herein can be used in any procedure that modifies aqueous fluid outflow. Non-limiting examples include glaucoma surgery, cataract surgery, and retinal surgery.

In some embodiments, a method includes inserting an infusion line into the tissue compartment of the subject, wherein the infusion line provides fluid communication between a fluid source and the tissue compartment of the subject; detecting a pressure within the tissue compartment over a time period; and performing an intervention on the subject based on the fluid outflow behavior of the tissue compartment determined from the pressure within the tissue compartment detected by the sensor over the time period. In some cases, the method further comprises generating a fluid outflow behavior signature based on the pressure within the tissue compartment detected by the sensor over the time period. The fluid outflow behavior signature can be indicative of the pressure biometry of the tissue compartment. In some cases, the method further comprises modifying the intervention based on a change in the fluid outflow behavior signature. The modification of the intervention can be performed to achieve a more desirable post-surgical fluidic outflow and pressure state.

In some embodiments, a method can include detecting the fluid outflow behavior of the tissue compartment over a time period, wherein the infusion line provides fluid communication between a fluid source and the tissue compartment of the subject; and generating a representation of the fluid outflow behavior of the tissue compartment. The representation can be a fluid outflow signature, pressure decay curve, or infusion response curve that is indicative of peri-operative or post-operative fluid balance state and dynamic resting pressure homeostasis.

Further described herein are methods, devices, and systems for monitoring dynamic changes in fluid outflow from the eye of a subject. The methods, devices, and systems can continuously monitor IOP changes associated with the dynamic fluid outflow behavior. During eye surgery (intra-operative phase), regulating the pressure inside the eye is critical for both the success of the surgery and reducing the likelihood of post-surgical complications. Regulation of IOP requires an assessment of ocular fluid outflow behavior, for example, by monitoring dynamic changes in fluid outflow that is associated with changes in IOP. The methods, devices, and systems described herein provide real-time guidance for taking appropriate actions to regulate fluid outflow behavior in real-time, e.g. during ocular surgery. Further, these methods, devices, and systems can determine whether a subject may be at risk of undesirable IOP post-operatively. Following ocular surgery (post-operative phase), patients can exhibit elevated IOP or reduced IOP, each of which can pose a risk to long-term ocular health. For example, abnormal fluid outflow behavior can result in vision loss or suboptimal post-operative IOP results. Early diagnosis of abnormal fluid outflow behavior allows for early intervention, thereby minimizing poor outcomes associated with undesirable IOP. For patients exhibiting abnormal ocular fluid outflow behavior, a post-operative office visit may be required to further monitor and assess IOP. Methods that improve control and prediction of post-operative fluid outflow behavior and IOP can reduce potentially unnecessary office visits.

Many devices used for measuring intra-operative IOP provide static pressure readings uncoupled to dynamic fluid or gas infusion, which do not provide a continuous, uninterrupted, dynamic characterization of IOP behavior based on fluid inflow/outflow homeostasis and outflow facility of the eye. Tonometry, i.e., Goldmann applanation tonometry, is the gold standard for measuring IOP. In applanation tonometry, IOP is inferred from the force required to flatten (or applanate) a constant area of the cornea. As with other non-invasive devices, this assessment of IOP can be inaccurate due to a number of factors, such as swelling in the cornea (corneal edema), which can be common during ocular surgery. Further, tonometry measures a static pressure reading and does not provide information about the dynamic outflow behavior of the eye. Thus, systems and devices described herein that characterize dynamic IOP behavior provide not only a more comprehensive assessment of ocular state, but a predictive intraoperative biometric paradigm which can guide surgical intervention for improved fluidic peri-operative and post-operative outcomes. These systems and devices can thereby provide a personalized, custom-tailored assessment of the unique fluidic balance and behavior of a patient, e.g., during surgery where modulating and predicting IOP is critical. These systems and devices can also provide treatment titratable to the unique fluidic behavior of patients.

Systems and devices described herein can be used to determine an appropriate size of an incision, pressure relief valve, or outflow conduit to be made in an ocular surgery. During ocular surgery, a small incision is made in the eye. Depending on the size of the incision, fluid outflow can increase moderately or significantly as a result. This change in fluid outflow can correspond to a moderate or significant decrease in IOP. For example, if the incision is large, fluid outflow can increase significantly, thereby resulting in a significant reduction in IOP. If the incision is small, fluid outflow can only increase moderately or not at all, thereby resulting in a minor change or no change in IOP. In addition to the magnitude change in fluid outflow, the rate of the resultant change can also be important for determining an appropriate incision size. For example, an incision that is too large can result in a rapid change in fluid outflow and can be associated with a characteristic shift of baseline fluid dynamics and the biometric pressure response curve. A small incision can result in a moderate change or no change in fluid outflow. In these cases, the incision can be enlarged to modulate fluid outflow or IOP of the eye. Based on a detected magnitude, rate, or pattern of fluid outflow, a surgeon can determine whether an outflow tract or stented pathway is too large and must be modified, whether an incision is too small and a larger incision can be made, or whether the incision size is sufficient and the surgery may proceed. In most cases, a small deviation in fluid outflow behavior or IOP is tolerable and does not pose a significant risk to the patient. A large deviation in IOP can indicate increased risk of injury or complications, which can be mitigated by modifying a procedure or aborting the surgery. Systems and devices described herein can be used to improve fluid outflow facility of an eye of a subject. These systems and devices can be used to assess pre-operative, intra-operative, or post-operative fluid outflow behavior of the eye. Based on a detected outflow behavior, an intervention can be performed to modulate fluid outflow facility, for example, by increasing or decreasing the rate or amount of fluid outflow. Interventions that modulate fluid outflow of the eye modulate the outflow pathway of the eye. Non-limiting examples of interventions that modulate fluid outflow of the eye include adjusting the size of an incision in the eye, adjusting incision flaps in the eye, adjusting a diameter of an infusion line inserted into the eye, modifying the size of a stent inserted into the eye, reducing the number of stents inserted into the eye, and increasing the number of stents inserted into the eye. In some embodiments, systems and devices described herein can be used to confirm that no intervention is required if the observed fluid outflow behavior is satisfactory.

In some embodiments, systems and devices described herein can be used to assess the functionality of other devices. For example, a system can be used to determine whether a valve of an ocular drainage device is functioning as desired. An Ahmed glaucoma valve implant is an implant used to promote fluid drainage in the eye to reduce IOP. The implant can be designed to regulate the IOP within an acceptable range, e.g., less than 14 mmHg. Systems and devices described herein can be used monitor dynamic IOP changes or fluid outflow behavior after implantation in a patient. Abnormal IOP changes or fluid outflow behavior can indicate that the implant is defective or requires modification.

Further described herein are methods of monitoring fluid outflow behavior of an eye of a subject, comprising: a) administering to the subject an intervention for modulating intraocular pressure; b) detecting an outflow of a fluid from the eye along an infusion line over a time period; and c) determining based on the detecting whether the intervention for intraocular pressure modulates the intraocular pressure in the subject. In some embodiments, the intervention is a pharmaceutical intervention that reduces intraocular pressure.

Further described herein are methods of monitoring fluid outflow behavior of an eye of a subject, comprising: a) performing an intervention for modulating intraocular pressure in the subject; b) detecting an outflow of a fluid from the eye along an infusion line over a time period; and c) determining based on the detecting whether the intervention for intraocular pressure modulates the intraocular pressure in the subject. In some embodiments, the intervention is an intervention that reduces intraocular pressure.

Glaucoma

According to World Health Organization, glaucoma is a leading cause of blindness globally. Approximately 10% of people with glaucoma who receive proper treatment still experience loss of vision, and there remains no cure for glaucoma. Medication and/or surgery can reduce the likelihood of further vision loss due to glaucoma, but disease progression must be monitored for life.

Open-angle glaucoma, also known as primary or chronic glaucoma, is the most common form of glaucoma, and accounts for more than 90% of all diagnosed cases. This form of glaucoma is characterized by the progressive clogging of the drainage canals in the eye, which results in increased IOP. "Open-angle" refers to the wide and open angle between the iris and the cornea, which is in contrast to angle-closure or narrow-angle glaucoma, a less common form of glaucoma. Angle-closure glaucoma is characterized by a closed or narrow angle between the iris and cornea, which contributes to the pathology of this type of glaucoma. Non-limiting examples of glaucoma include open-angle glaucoma, close-angle glaucoma, narrow-angle glaucoma, primary glaucoma, secondary glaucoma, wide-angle glaucoma, congenital glaucoma, acquired glaucoma, pigmentary glaucoma, pseudoexfoliative glaucoma, primary juvenile glaucoma, traumatic glaucoma, inflammatory glaucoma, phacogenic glaucoma, and neovascular glaucoma.

Under normal conditions, aqueous humor (fluid) in the eye freely flows through the anterior chamber and exits through the trabecular meshwork (drainage canals) and uveoscleral pathways (reabsorption by and diffusion into surrounding tissues). In glaucoma, aqueous humor accumulates due to inadequate drainage, thereby increasing pressure within the eye. Elevated pressure in the eye can lead to damage of the optic nerve and gradual vision loss.

Although the damage caused by glaucoma is generally irreversible, glaucoma patients can undergo interventions to reduce the likelihood of and/or slow the progression of further damage and permanent vision loss. These interventions include agents that reduce intraocular pressure, increase fluid drainage in the eye, and/or reduce the production of aqueous humor. Non-limiting examples of glaucoma pharmaceutical interventions include prostaglandins, beta blockers, carbonic anhydrase inhibitors, Rho kinase inhibitors, miotic agents, and cholinergic agents. Additional glaucoma interventions include laser therapy and surgery, which improve aqueous humor outflow, thereby reducing intraocular pressure. In some embodiments, a surgeon can recommend a glaucoma patient to undergo pharmaceutical interventions, such as those described herein, to control and manage IOP following glaucoma surgery.

Laser Therapies

Selective laser trabeculoplasty (SLT) is a procedure used for the treatment of primary open-angle glaucoma (POAG). SLT involves the use of a laser beam to open clogged channels in the trabecular meshwork. This procedure selectively targets specific cells of the trabecular meshwork, while keeping untreated cells intact. For this reason, SLT can be performed in glaucoma patients repeatedly. SLT can be an alternative for those who have been treated unsuccessfully with ALT or pressure-lowering eye drops.

Argon laser trabeculoplasty (ALT) is also used for the treatment of POAG. Similar to SLT, ALT involves the use of a laser beam to open fluid channels of the eye, thereby improving fluid drainage. Typically, half the fluid channels are treated initially. As necessary, additional fluid channels can be treated in a separate session at a later time. This strategy prevents over-correction and reduces the risk of increased ocular pressure following surgery. In many cases, additional medications are needed in conjunction with ALT.

Laser peripheral iridotomy (LPI) is used for the treatment of narrow angles and narrow-angle glaucoma. Narrow-angle glaucoma (also known as angle-closure glaucoma) occurs when the angle between the iris and the cornea in the eye is too small. The reduced area causes the iris to block fluid drainage, thereby increasing IOP. In LPI, a tiny hole is introduced in the iris that allows the iris to fall away from the drainage area inside the eye, thereby opening the angle and providing an alternate drainage pathway if the angle closes or drainage is blocked.

Laser cyclophotocoagulation is an alternative to filtering microsurgery that is typically recommended later in the treatment algorithm of glaucoma. In this procedure, several different types of lasers are used to inhibit the ciliary body's ability to produce aqueous humor, thereby preventing fluid accumulation and lowering IOP. In some cases, this procedure must be repeated multiple times to effectively control glaucoma.

Incisional Procedures

Trabeculectomy is a surgical procedure that makes a small incision in the eye wall (sclera) to amplify outflow and reduce homeostatic balance between aqueous production and aqueous outflow which results in a lower state of IOP. Some of the mesh of tissue inside the eye is removed and a flap is created over the hole to allow drainage of fluid in a controlled manner. In some cases, additional medication is required in conjunction with this surgery to manage and reduce the likelihood of scar tissue formation.

In drainage implant surgery, a tiny tube can be placed into the eye to allow fluid drainage, amplify aqueous outflow, and reduce homeostatic balance between aqueous production and outflow, which results in reduced IOP. This procedure is more controlled compared to trabeculectomy and may be preferable if extensive scarring of the outer layers of the eye is expected, but may not provide as low IOP as trabeculectomy. Minimally invasive implants have been developed for drainage implant surgeries.

Electrocautery, or thermal cautery, is a procedure that involves the use of an electrical heating device called a Trabectome®. In this procedure, a tiny incision is made in the drainage tubes of the eye. The heating device is inserted into the eye to heat to trabecular meshwork, thereby reducing fluid buildup and IOP. This procedure is less invasive than both trabeculectomy and drainage implant surgery.

Additional non-limiting examples of glaucoma procedures or devices for use therein and corresponding estimated reductions in IOP are listed in TABLE 1.

TABLE 1

| Outflow Pathway | Surgery | IOP Reduction |
| --- | --- | --- |
| Subconjunctival | Trabeculectomy | 49.5% at 5 years |
| | Aqueous shunt | 41.4% at 5 years |
| | Ex-PRESS ® | 44% at 2 years |
| | XEN ® | 36.4% at 1 year |
| Trabecular | iStent inject ®* | 20% at 1 year |
| | Hydrus ®* | 36% at 2 years |
| | Trabectome | 52% at 1 year |
| Suprachoroidal | CyPass ®* | 30% at 2 years |

*Combined with cataract surgery

Dynamic Intra-Operative Outflow Systems

As discussed above, the main purpose of glaucoma surgery is to augment the homeostatic outflow capacity of the intraocular compartment, thereby reducing baseline IOP in the eye. However, how well a surgery achieves reduction in IOP can be difficult to assess as there are no intra-operative biometric tools to measure baseline outflow capacity and the effect of an ocular intervention. Additionally, following eye surgery (the post-operative period), patients may have abnormally high IOP or abnormally low IOP, each of which can pose dangerous risks to the patient. Normal IOP ranges from about 12-22 mmHg. As much as 28% of cataract surgery patients with co-morbid glaucoma demonstrate abnormally high IOP that is over 30 mmHg and more than 50% of these patients experience IOP that is over 25 mmHg. Even for routine cataract surgery patients without glaucoma co-morbidity, about 10% of these patients experience high IOP that is over 30 mmHg on post-operative Day 1 after surgery, and 6% of patients experience very low IOP that is below 5 mmHg.

Abnormal post-operative IOP is even more common in patients that undergo glaucoma surgery, such as trabeculectomy, shunt surgery, or micro-stents. In trabeculectomy, for example, the rate of hypotony (low IOP) can exceed 30%, which poses a significant risk of follow-on complications.

Abnormal IOP fluctuations also place patients at risk for vision loss or suboptimal post-operative results. Monitoring IOP fluctuations is the main reason for Day 1 post-operative cataract and glaucoma patient office visits. Methods, devices, and systems that can identify high-risk patients and reduce the likelihood of IOP spikes and abnormal IOP can reduce the frequency of office visits.

There are currently no clinically useful biomarkers for predictive fluid outflow and IOP management of patients undergoing intraocular surgery. While discrete pre-operative, peri-operative, and intra-operative IOP measurements can be obtained with standard, currently available devices, these static measurements do not closely correlate with the eye's outflow facility, the most important factor in determining IOP homeostasis following surgery. Conventional devices are also uncoupled to intraoperative fluid infusion or decay monitoring and thus, are unable to inform or predict resting aqueous outflow dynamics and ocular outflow capacity, especially in real-time during surgery. In addition, the most common devices used to measure IOP, tonometers, can lead to inaccurate readings due to various factors, including corneal edema, a common occurrence during eye surgery. The current standard for assessing intra-operative outflow during surgery is visual and tactile inspection by the surgeon. That is, the surgeon visually monitors the amount of fluid egress through an outflow tract, such as an incision, and palpates the eye to predict whether the amount of fluid outflow is too much, too little, or acceptable. This technique can be subjective and does not provide a comprehensive understanding of the intraocular fluid outflow behavior and pressure regulation in a dynamic system such as the eye.

Described herein are methods, devices, and systems for intra-operative dynamic outflow assessment, which can provide a surgeon with immediate biometric information to estimate the outflow facility of the eye. These methods, devices, and systems can characterize the eye's outflow in real-time to guide surgeons make modifications during surgery when interventions are safe and convenient. These methods, devices, and systems allow surgeons to better predict whether a patient is at a risk for undesirable post-operative IOP so that more informed surgical and clinical decisions regarding the patient's care can be made.

Systems and devices described herein include an infusion line, a sensor, and a processor. An infusion line can be placed into an eye of a subject to provide fluid communication between a fluid source and the eye. The infusion line can provide controlled micro-volumetric delivery of a fluid to the eye, which can be used in fluid challenge testing.

In some embodiments, the infusion line can be fluid communicatively coupled to the eye through a probe, for example, a catheter or needle. In some embodiments, the probe has a self-sealing entry port. In some embodiments, the probe can inject a microvolume of a fluid into the eye. In some embodiments, the probe and the sensor are in a common housing, i.e., the probe and the sensor are coaxial. In some embodiments, the sensor is an intraocular sensor. In some embodiments, the sensor is coaxial with the infusion line, but is remote from the probe, i.e., extraocular. In alternative embodiments, the probe and the sensor are not coaxial, i.e., the sensor is an extraocular sensor. In these embodiments, the sensor is remote from the probe. In some embodiments, the system or device further comprises a handpiece that combines the probe and sensor to facilitate insertion of the device through an incision in the eye. In some embodiments, the probe further includes a blade or needle that is configured to make an entry into the eye. In some cases, insertion of the probe is through an existing incision made during the surgery.

Minimizing anatomic obstruction of the dynamic outflow device can be desirable, for example, during use in intraocular surgery. Because the eye is a soft, pliable tissue, accidental maneuvering of the probe during an intraocular procedure can distort the shape of the eye. As a result, the distortion can damage the eye, affect the detected IOP or fluid outflow behavior, and interfere with the procedure. To reduce the likelihood of ocular damage and minimize obstruction, the probe of a device described herein can comprise a very short entry needle. A small entry needle can prevent ocular damage (e.g., iris damage) and minimize anatomic obstruction during surgery. In some embodiments, the needle only penetrates through the cornea and does not penetrate into deeper regions in the eye. For example, the entry needle can be about 100 μm to about 5000 μm in length. In some embodiments, the entry needle can be less than 100 μm.

In some embodiments, the infusion line is designed to minimize surgical interference or obstruction to visualization and maneuverability during eye surgery. The probe can be a port having a short, hollow-bore, self-sealing needle affixed to a head and the infusion line. The probe is configured to be relatively small such that the probe does not distort the eye or IOP measurements. For example, the probe can be a perforating transcorneoscleral tip. This incisional entry tip can be coupled with the infusion-tonometry line to provide a sealed, leak-free system for accurate measurement of outflow. The needle can be attached to the head at an angle such that the needle permits the head and infusion line to be non-obtrusive to the surgeon, instrumentation, or other ocular structures. For example, the head can be flat against the external surface of an ocular compartment (e.g., sclera) to which the needle enters. The needle can be perpendicular to the head, such that the head and infusion line are flat against the surface of the eye. Upon insertion of the needle port into the eye, the head can remain external to the eye. In some embodiments, the probe is a transcorneoscleral port. In some embodiments, the probe is leak-proof and non-distortive to surrounding structures. The intraocular portion can be configured to gain entry to a cavity, such as the anterior chamber, but to avoid impact to anterior chamber structures, such as the iris or lens, or intraocular surgical instrumentation. In some embodiments, the port can be removed and re-inserted, e.g., during surgery. In some embodiments, the port is inserted into the eye for the duration of a procedure.

The infusion line, or the probe connected to the infusion line, can be inserted into various parts of the eye, for example, the cornea, sclera, anterior chamber, posterior chamber, vitreous chamber, or any ocular tissue structure that compartmentalizes the pressurized bio-chamber. Additional non-limiting parts of the eye in which a device described herein can be inserted include anterior segment, posterior segment, sub-Tenon's space, subconjunctival space, intraconal space, retrobulbar space, extraconal space, orbit, lacrimal sac/system and other adnexal tissues of the eye and orbit, optic nerve sheaths, ethmoidal, maxillary, frontal, and sphenoidal sinuses. Intraocular pressure can be dynamically monitored based on a volume of the fluid that exits the eye via the conventional (trabecular) outflow pathways or unconventional (uveoscleral or uveovortex) outflow pathways. The outflow behavior of the eye can correspond to changes in the intraocular pressure of the eye, for example, during the course of a medical procedure.

Dynamic intraocular pressure of the eye can be detected by a pressure sensor. In some embodiments, the sensor can be located along the infusion line. In these embodiments, the pressure sensor is co-axial with the infusion line. In some embodiments, the sensor is an intraocular pressure sensor. For example, the sensor is located on a probe that is inserted into the eye, such that the probe can telescope into the eye. In some cases, fluid outflow can be detected based on a volume change or a pressure change detected by the sensor. The sensor is configured to detect intraocular pressure continuously and/or in real-time. In some embodiments, the sensor is a pressure sensor. In some embodiments, the sensor is a nanomaterial-based pressure sensor, for example, a microscale nanodot-enhanced sensor. A pressure sensor can contain a nanodot-embedded deformable silicon nitride (SiN) membrane and a silicon reflective surface. The nanodot-enhanced IOP sensor can be positioned in the anterior chamber of the eye and actuated using near-infrared light. IOP can be measured based on a shift in the sensor-reflected resonance as a function of the gap distance within the sensor's optical cavity. In some embodiments, the sensor is non-invasive, for example, is not inserted into the eye or a tissue compartment. In some embodiments, the sensor is an extraocular pressure sensor. For example, the sensor is located along the infusion line, but remote from the eye of a subject.

In some embodiments, the sensor can be configured to detect intraocular pressure-based fluid outflow for a duration of an intervention, procedure, or surgery being performed on a subject, prior to the intervention performed on the subject, or following the intervention performed on the subject. In some cases, the device can be used independent of an intervention. Prior to eye surgery, dynamic fluid outflow can help determine whether proceeding with the surgery is appropriate, i.e., determining a risk of complications associated with IOP. During surgery, dynamic fluid outflow can inform whether a modification of a procedure may be warranted to reduce risk of injury or other complications. Following surgery, dynamic fluid outflow behavior can be used to characterize success of the surgery and prognose complications that require additional interventions or further diagnostic testing. Thus, methods that characterize dynamic fluid outflow behavior of the eye can significantly improve recovery time for ocular surgery patients.

In a situation where there is a leakage in the eye, an increase in fluid outflow can be detected by the pressure sensor, thereby indicating a decrease in IOP or a flattened dynamic pressure curve. If fluid outflow is stable, then the IOP will also be consistent. In cases where IOP increases, for example, due to of fluid accumulation in the eye or reduced fluid outflow from the eye, a decrease in fluid outflow can be detected by the sensor, thereby indicating an increase in IOP. Based on detected changes in IOP (and thus, fluid outflow), a surgeon can perform an intervention or modify a procedure of the surgery. For example, the intervention or modified procedure can be performed to induce a change in fluid outflow behavior. In some embodiments, an action is not taken in response to the detected fluid outflow from the eye. In such cases, the surgeon can proceed with a planned procedure because no imminent, peri-operative, or post-operative risk is detected based on the inferred IOP/fluid outflow behavior.

The pressure sensor can be communicatively coupled to a computer system comprising a processor. In some embodiments, the processor is communicatively coupled to the sensor through the infusion line. The processor can be configured to receive and process data associated with the intraocular pressure of the eye. Further, the processor can generate a representation of the fluid outflow behavior pattern based on the received and processed IOP data. The representation can be generated concurrently with detection of the IOP. Thus, the representation can be generated continuously and in real-time as the sensor detects IOP continuously and in real-time. The representation of the fluid outflow behavior can be visual, audial, and/or tactile (haptic). In some embodiments, the representation of the fluid outflow behavior is a graphical representation on a visual display, e.g., a graphical representation of the fluid outflow behavior pattern over time. The graphical representation can display the IOP behavior of the eye over time. A visual display can indicate whether a fluid outflow pattern is normal or abnormal, e.g., by color-coding or pop-up notifications. In some embodiments, the representation of the fluid outflow behavior is audial. For example, when a fluid outflow pattern is detected as abnormal by the system, an audial alert can be triggered to notify a user, such as the operating physician. In some embodiments, the system provides haptic feedback corresponding to the fluid outflow behavior.

In some embodiments, the processor can process the received data and provide a diagnostic assessment of the fluid outflow or IOP behavior and/or a corresponding clinical recommendation. The fluid outflow behavior can be characterized by analyzing pressure data patterns or critical values. This characterization can be in the form of, but not limited to, graphical representations, numerical values, formulae, and algorithms. The system can make predictions or recommendations based on the characterization. These predictions or recommendations can include diagnostic predictions, prognostic predictions, approval of the fluidic behavior, disapproval of the fluidic behavior, or recommendations of possible medical interventions to modulate the fluid behavior. A surgeon can modify and refine these recommendations as needed.

The system can also identify clinical signatures or features based on the processed IOP data. For example, if a particular pattern, e.g., a valve effect, is identified by the system, then the system can generate a specified comment, such as a notification indicating as such. In another example, if a desired pressure, such as a critical pressure, is reached, then the system can generate a notification indicating as such.

Figure 10:
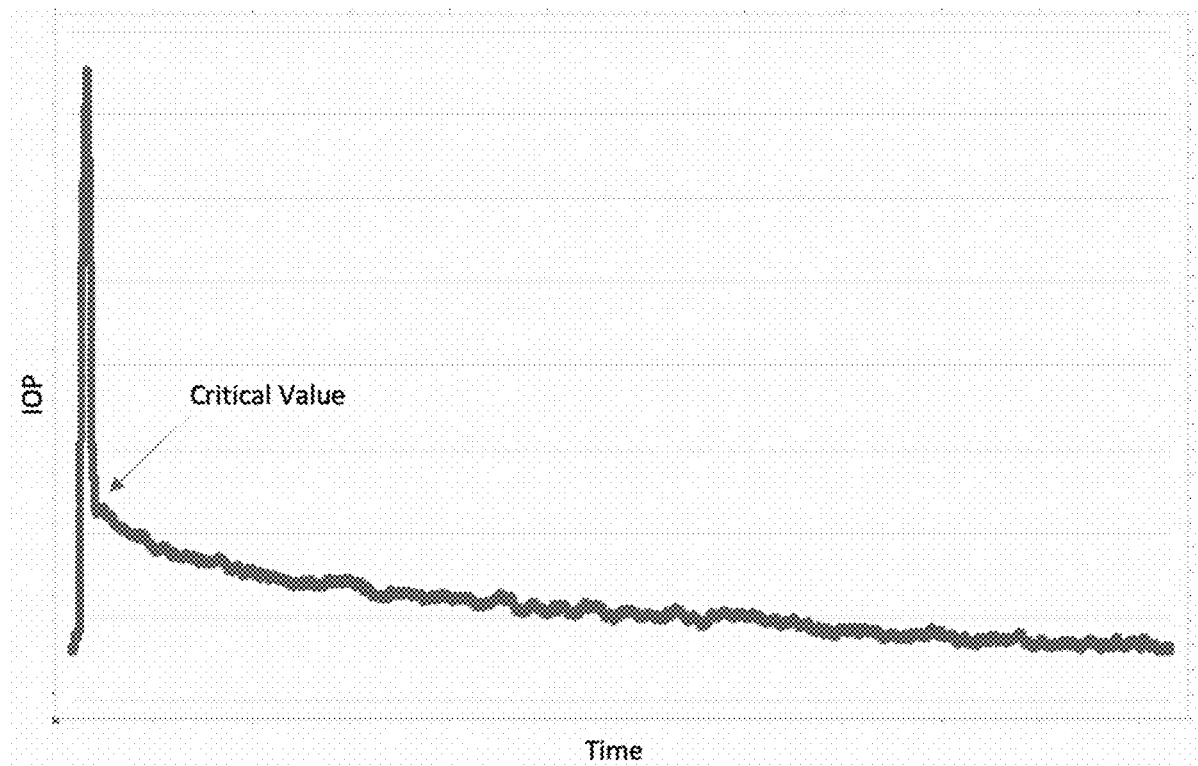
FIG. 10 illustrates an example fluid outflow curve showing a critical value notification.
Figure 11:
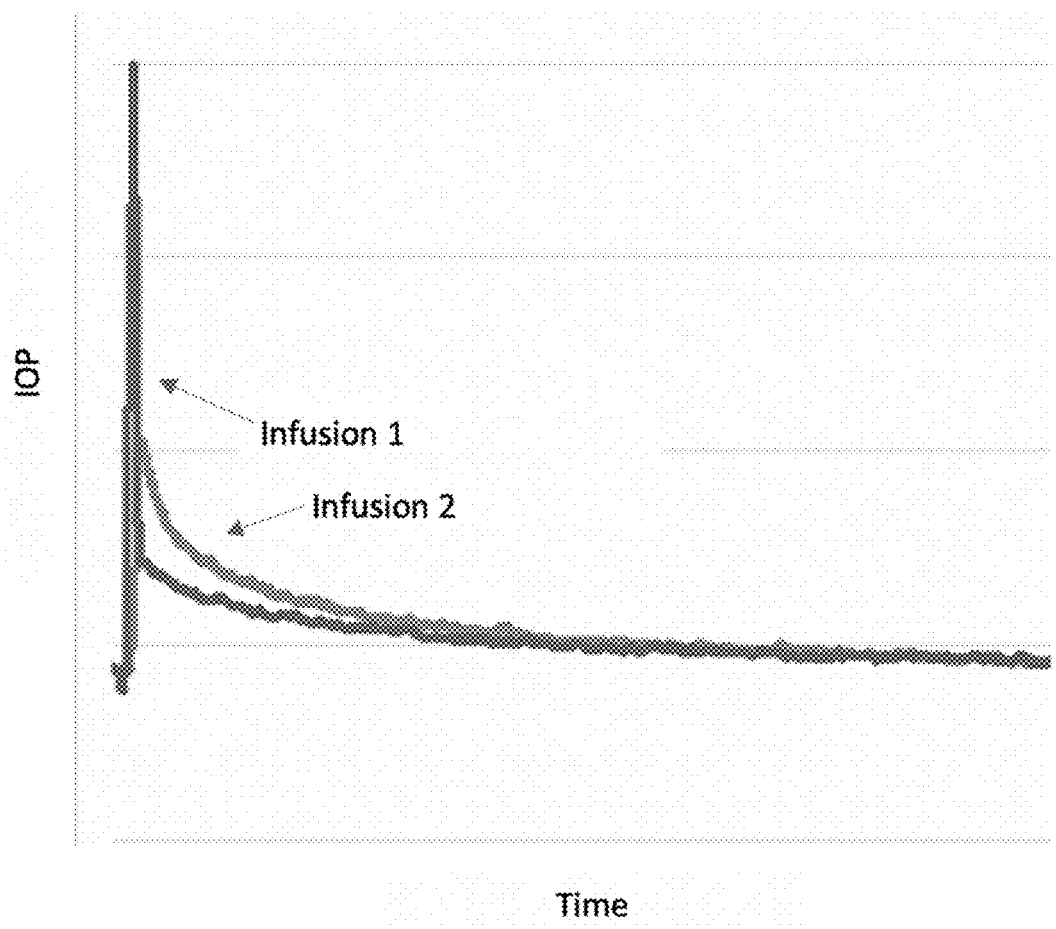
FIG. 11 illustrates an example fluid outflow curve showing the fluid behavior from two separate infusions.
Figure 12:
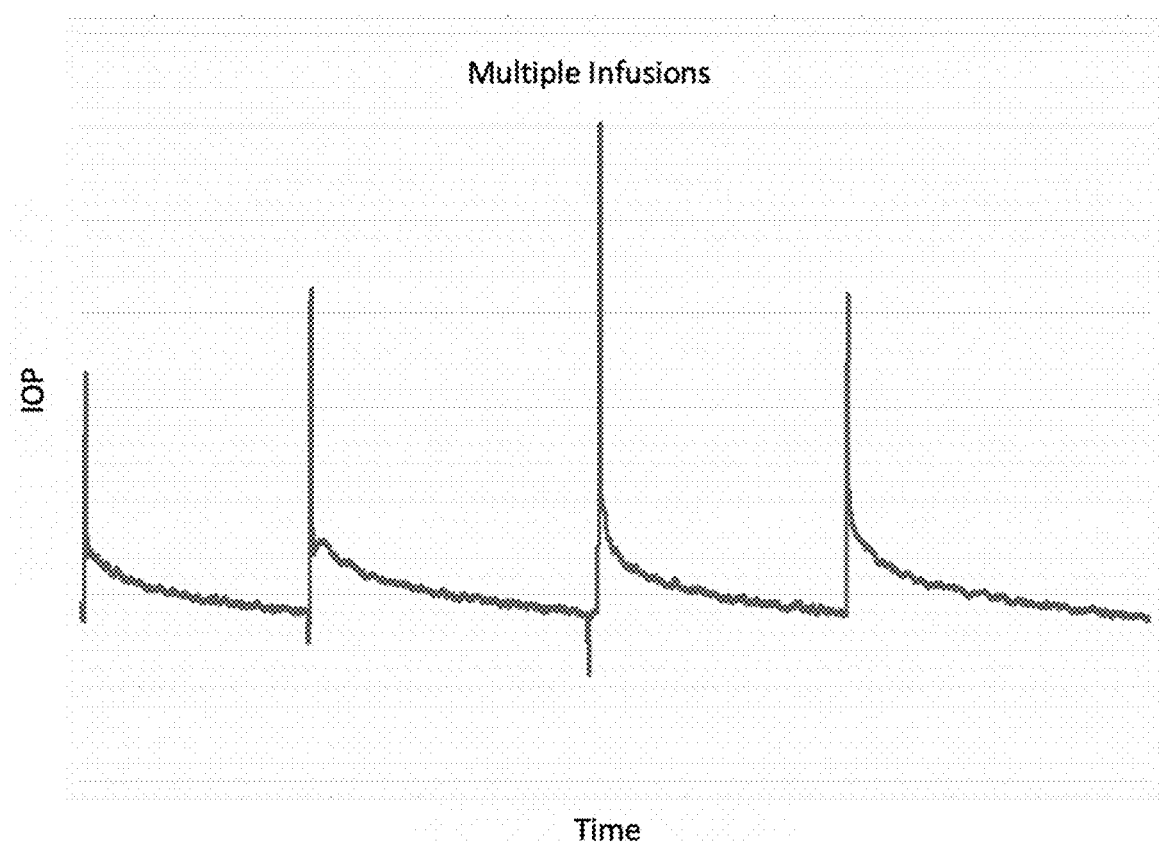
FIG. 12 illustrates an example fluid outflow curve showing multiple infusions of varying volumes.

FIG. 10 illustrates an example graphical representation showing a critical value notification. FIG. 11 illustrates an example graphical representation showing the fluid behavior from two separate infusions. In this example, the first infusion pattern is a baseline fluid behavior; the second infusion is the fluid behavior following a surgical modification or IOP intervention. In this way, the system can provide a visual comparison of pre- and post-surgical modification IOP/outflow behavior. FIG. 12 illustrates an example graphical representation of the fluid behavior after multiple infusions of varying volumes. The system can also modify parameters of an infusion, including, but are not limited to, starting IOP/outflow of infusion, ending IOP/outflow of infusion, peak and trough IOP/outflow of infusion, a target IOP/outflow or parameter, such as maintaining a specified constant rate of infusion.

The processor can also be configured to store data received from the sensor, for example, in a memory. In some cases, the processor can be configured to transmit data associated with the fluid outflow behavior, for example, to another computer processor for additional processing, analysis, or storage. In some embodiments, the system includes a display that is configured to electronically display a graphical representation of the fluid outflow behavior. The display can be communicatively coupled to the processor. The graphical representation can be displayed concurrently with detection of the fluid outflow continuously and/or in real-time. In some embodiments, the processor and the display are in a common housing.

In some embodiments, a computer system can receive data associated with the fluid outflow behavior of an eye of a subject. The received data can then be compared by a processor of the computer system to a reference to determine whether the fluid outflow behavior is indicative of risk, condition, or symptom. Non-limiting examples of references that can be used by the computer system include historical IOP measurements or behavior patterns from the subject, IOP measurements or behavior patterns from a healthy subject (having normal IOP measurements or behavior), statistical IOP measurements or behavior patterns associated with a condition, and reference texts. The computer system can then output a result of the determination.

In some embodiments, systems and devices described herein include a processor coupled to a transmitter configured to transmit data from the device to a remote location, for example, a remote processor in a hospital, a clinic, or a doctor's office. The transmitter can be configured to transmit data wirelessly, for example, via Bluetooth®, wireless networks, cell phone networks, a cloud network, or the internet. For example, the device can use Bluetooth® to connect to an analysis device, including but not limited to, a mobile device, tablet, cell phone, or computer system. In some embodiments, the transmission is wired. The processor can be configured to transmit data to a plurality of receivers in a plurality of geographic locations.

Systems and devices described herein can also include a pump that is configured to actuate or modulate flow of a replacement fluid to the eye of the subject. During surgery, fluid supplementation to the eye can be required to maintain a normal IOP range, for example, after an incision in the eye is made or when tissue is removed from the eye. The replacement fluid can be a saline solution, a pH balanced solution, or any solution suitable for modulating IOP in the eye. The pump can include a fluid source that contains the replacement fluid. The pump can be communicatively coupled to the infusion line, the sensor, or the processor. In some embodiments, the processor is communicatively coupled to the pump, such that the processor actuates and controls the pump. For example, the processor can modulate a flow rate of the fluid into the eye that is generated by the pump. In some embodiments, the pump can be responsive to sensor data and can actuate multiple serial discrete micro-infusions. For example, sensor data can modify the method of infusion, e.g., the volume of fluid infused or the number of infusions. Based on the sensor data, one micro-infusion can be actuated, multiple micro-infusions can be actuated, or no micro-infusion is actuated through the pump.

Fluid Challenge Testing

Systems and devices described herein can also be used to characterize fluid outflow behavior by fluid challenge (or pressure challenge outflow) testing. Fluid challenge testing is performed to evaluate the behavior of the eye in response to an externally applied pressure, e.g., by fluid infusion. A volume of fluid can be infused into the eye over a period of time. The resultant change in outflow behavior in response to the infusion can be used to characterize IOP behavior, e.g., as a graphical representation of continuous, real-time fluctuations in fluid outflow. This representation can guide determination of whether a modification of a procedure or additional intervention is required. For example, an infusion that does not result in a significant change to fluid outflow can indicate that IOP behavior of the eye is favorable enough for the procedure to proceed without modification. Conversely, an infusion that results in a significant or rapid change to fluid outflow can indicate that there is a leakage in the eye and further intervention is warranted to mitigate the leakage and control fluid outflow and IOP. During fluid challenge testing, the volume of fluid infused into the eye can be varied to assess corresponding effects on IOP and fluid outflow, thereby inferring effects on peri- and post-procedural IOP and outflow behavior that is specific to a patient.

Further, in response to IOP changes during the course of a procedure, fluid can be infused into the eye to maintain a constant rate of fluid outflow and reduce extreme fluctuations in fluid outflow. For example, a reduction in IOP caused by reduced fluid flow, e.g., from a leak in the eye, can be ameliorated by infusion of fluid to the eye via the infusion line. A pressure sensor can detect the changes in outflow behavior and transmit the data to a processor, which processes the information to produce a representation of the response in real-time. Depending on a trend or behavior of the fluid outflow that is characterized by the representation, modifications to an intervention as deemed necessary by a physician can be made. In some embodiments, a fluid challenge test can be performed manually by injecting fluid by hand through a syringe, or automatically by a system or device described herein. In some embodiments, automatic injection of the fluid is preferable because manual injection can be variable and imprecise.

In some embodiments, the volume of the fluid infused to the eye can range from about 1 nL to about 100 nL, about 100 nL to about 1 µL, about 1 µL to about 50 µL, about 5 µL to about 30 µL, or about 10 µL to about 25 µL. In some embodiments, the volume of the fluid can be about 1 µL, about 2 µL, about 3 µL, about 4 µL, about 5 µL, about 6 µL, about 7 µL, about 8 µL, about 9 µL, about 10 µL, about 11 µL, about 12 µL, about 13 µL, about 14 µL, about 15 µL, about 16 µL, about 17 µL, about 18 µL, about 19 µL, about 20 µL, about 21 µL, about 22 µL, about 23 µL, about 24 µL, about 25 µL, about 26 µL, about 27 µL, about 28 µL, about 29 µL, about 30 µL, or more.

In some embodiments, infusion fluid or replacement fluid is a saline solution, a pH balanced solution, or any solution suitable for the eye.

Computer Systems

An aspect of the disclosure provides a system that is programmed or otherwise configured to implement the methods of the disclosure. The system can include a computer server that is operatively coupled to a computer processor.

FIG. 1 shows a computer system 100 programmed or otherwise configured to allow, for example, a user to view an electronic display of a graphical representation of dynamic fluid outflow behavior of an eye of a subject. The system 100 includes a computer server ("server") 101 that is programmed to implement methods disclosed herein. The server 101 includes a central processing unit (CPU) 102, which can be a single core or multi-core processor, or a plurality of processors for parallel processing. The server 101 also includes: memory 103, such as random-access memory, read-only memory, and flash memory; electronic storage unit 104, such as a hard disk; communication interface 105, such as a network adapter, for communicating with one or more other systems; and peripheral devices 106, such as cache, other memory, data storage and electronic display adapters. The memory 103, storage unit 104, interface 105 and peripheral devices 106 are in communication with the CPU 102 through a communication bus, such as a motherboard. The storage unit 104 can be a data storage unit or data repository for storing data. The server 101 can be operatively coupled to a computer network 107 with the aid of the communication interface 105. The network 107 can be the Internet, an internet or extranet, or an intranet or extranet that is in communication with the Internet. The network 107 in some cases is a telecommunications network or data network. The network 107 can include one or more computer servers, which can allow distributed computing, such as cloud computing. The network 107, in some cases with the aid of the server 101, can implement a peer-to-peer network, which can allow devices coupled to the server 101 to behave as a client or an independent server.

The storage unit 104 can store files, such as drivers, libraries, saved programs, and data related to a subject. The storage unit 104 can store data from, for example, fluid outflow data, intraocular pressure data, electronic health records, biometrics, contact information, and medical history. The server 101 in some cases can include one or more additional data storage units that are external to the server 101, such as located on a remote server that is in communication with the server 101 through an intranet or the Internet.

The server 101 can communicate with one or more remote computer systems through the network 107. In some embodiments, the server 101 is in communication with a first computer system 108 and a second computer system 109 that are located remotely with respect to the server 101. The first computer system 108 can be the computer system of a user, and the second computer system 109 can be an external data repository. The first computer system 108 and second computer system 109 can be, for example, personal computers, such as a portable PC; slate and tablet PC, such as Apple® iPad and Samsung® Galaxy Tab; telephones; smartphones, such as Apple® iPhone, Android-enabled device, Windows® Phone, and Blackberry®; smart watches, such as Apple® Watch; smart glasses, such as Google® Glass; or personal digital assistants. The user can access the server 101 via the network 107 to view a display of the invention.

In some embodiments, the system 100 includes a single server 101. In other situations, the system 100 includes multiple servers in communication with one another through an intranet or the Internet. The server 101 can be adapted to store event information, such as, for example, statistical data, video footage, external conditions, and other information of potential relevance to the event. Such event information can be stored on the storage unit 104 of the server 101.

Methods as described herein can be implemented by way of a machine- or computer-executable code or software stored on an electronic storage location of the server 101, such as, for example, on the memory 103 or electronic storage unit 104. During use, the code can be executed by the processor 102. In some embodiments, the code can be retrieved from the storage unit 104 and stored on the memory 103 for ready access by the processor 102. In some embodiments, the electronic storage unit 104 can be precluded, and machine-executable instructions are stored on memory 103. Alternatively, the code can be executed on the second computer system 109. The code can be pre-compiled and configured for use with a processor adapted to execute the code, or can be compiled during runtime. The code can be supplied in a programming language that can be selected to allow the code to execute in a precompiled or as-compiled fashion.

All or portions of the software can at times be communicated through the Internet or various other telecommunications networks. Such communications can support loading of the software from one computer or processor into another, for example, from a management server or host computer into the computer platform of an application server. Another type of media that can bear the software elements includes optical, electrical, and electromagnetic waves, such as those used across physical interfaces between local devices, through wired and optical landline networks and over various air-links. The physical elements that carry such waves, such as wired or wireless links, or optical links, also can be considered as media bearing the software.

A machine-readable medium, incorporating computer-executable code, can take many forms, including a tangible storage medium, a carrier wave medium, and physical transmission medium. Non-limiting examples of non-volatile storage media include optical disks and magnetic disks, such as any of the storage devices in any computer, such as can be used to implement the databases of FIG. 1. Volatile storage media include dynamic memory, such as a main memory of such a computer platform. Tangible transmission media include coaxial cables, copper wire, and fiber optics, including wires that comprise a bus within a computer system. Carrier-wave transmission media can take the form of electric or electromagnetic signals, or acoustic or light waves such as those generated during radio frequency (RF) and infrared (IR) data communications.

Common forms of computer-readable media include: a flash disk, a flexible disk, hard disk, magnetic tape, any other magnetic medium, a CD-ROM, DVD or DVD-ROM, any other optical medium, punch cards, paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, and any other medium from which a computer can read programming code or data. Many of these forms of computer readable media can be involved in carrying one or more sequences of one or more instructions to a processor for execution.

Computer software can include computer programs, such as, for example executable files, libraries, and scripts. Software can include defined instructions that upon execution instruct computer hardware, for example, an electronic display to perform various tasks, such as display graphical elements on an electronic display. Software can be stored in computer memory.

Software can include machine-executable code. Machine-executable code can include machine language instructions specific to an individual computer processor, such as a CPU. Machine language can include groups of binary values signifying processor instructions that change the state of an electronic device, for example, a computer, from its preceding state. For example, an instruction can change the value stored in a particular storage location inside the computer. An instruction may also cause an output to be presented to a user, such as graphical elements to appear on an electronic display of a computer system. The processor can carry out the instructions in the order they are provided.

Software comprising one or more lines of code and their output(s) can be presented to a user on a user interface (UI) of an electronic device of the user. Non-limiting examples of UIs include a graphical subject interface (GUI) and web-based subject interface. A GUI can allow a subject to access a display of the invention. The UI, such as GUI, can be provided on a display of an electronic device. The display can be a capacitive or resistive touch display, or a head-mountable display, such as a Google® Glass. Such displays can be used with other systems and methods of the disclosure.

Any embodiment of the invention described herein can be, for example, produced and transmitted by a user within the same geographical location. A product of the invention can be, for example, produced and/or transmitted from a geographic location in one country and a user of the invention can be present in a different country. In some embodiments, the data accessed by a system of the invention is a computer program product that can be transmitted from one of a plurality of geographic locations to a user. Data generated by a computer program product of the invention can be transmitted back and forth among a plurality of geographic locations, for example, by a network, a secure network, an insecure network, an internet, or an intranet. In some embodiments, a system herein is encoded on a physical and tangible product.

Subjects

Systems, devices, and methods can be applied to a subject in need thereof. For example, the subject is afflicted with an ocular condition. Non-limiting examples of ocular conditions include glaucoma, ocular hypertension, hypotony, cataracts, diabetic retinopathy, macular degeneration, ocular edema, macular edema, corneal edema, retinal detachments, macular pucker, corneal scarring or ulceration, ruptured globe, optic neuritis, retrobulbar hemorrhage, lacrimal system tumors/abscesses, sinus tumors/abscesses, congenital deformities or conditions, trauma, ocular cancer, benign neoplasms, any ocular condition, such as those described herein.

The subject can be undergoing a medical procedure, e.g., an in-office procedure or a surgery. The subject can be undergoing an ocular procedure. A subject can be a candidate for or undergoing an ocular surgery, including, but not limited to, glaucoma surgery, cataract surgery, corneal surgery, retinal surgery, vitrectomy, diabetic retinopathy surgery, macular degeneration surgery, laser-assisted in situ keratomileusis (LASIK), photorefractive keratectomy (PRK), orbital surgery, retinal detachments repair, membrane peel, corneal transplant, ruptured globe repair, optic nerve sheath fenestration, canthotomy, cantholysis, lacrimal system tumors/abscesses repair/biopsy/excision/treatment, sinus tumors/abscesses repair/biopsy/excision/treatment, repair or treatment of congenital deformities or conditions, trauma repair, ocular cancer repair/biopsy/excision/treatment, benign neoplasms repair/biopsy/excision/treatment, any ocular surgery, or any ocular procedure, such as those described herein.

The subject can be a human, an animal, a domesticated animal, a zoo animal, a cow, a horse, a pig, a sheep, a mouse, a rat, a rabbit, a dog, a cat, or a monkey.

Systems, devices, and methods described herein can detect a wide range of intraocular pressures in a subject. Systems and devices described herein can be used to detect physiological IOP in a subject. For example, systems described herein can detect IOP from about 5 mmHg to about 30 mmHg in a human. In some embodiments, systems described herein can detect IOP below 5 mmHg. In some embodiments, systems described herein can detect IOP above 30 mmHg.

Systems and devices described herein can be used for dynamic intraocular pressure sensing to provide continuous uninterrupted tonometry and/or continuous fluid outflow behavior for a time period. In some embodiments, a time period is at least 1 second, at least 2 seconds, at least 3 seconds, at least 5 seconds, at least 10 seconds, at least 15 seconds, at least 20 seconds, at least 30 seconds, or more. In some embodiments, a time period is about 10 minutes, about 20 minutes, about 30 minutes, about 40 minutes, about 50 minutes, about 60 minutes, or more. In some embodiments, a time period is less than a second, less than a minute, or less than an hour. In some cases, the time period is a duration of a procedure being performed on the eye of a subject, e.g., a surgical procedure. In some cases, the time period is any detection period desired by a user of the device.

EXAMPLES

Example 1. Systems for Monitoring Dynamic Fluid Outflow

Figure 2:
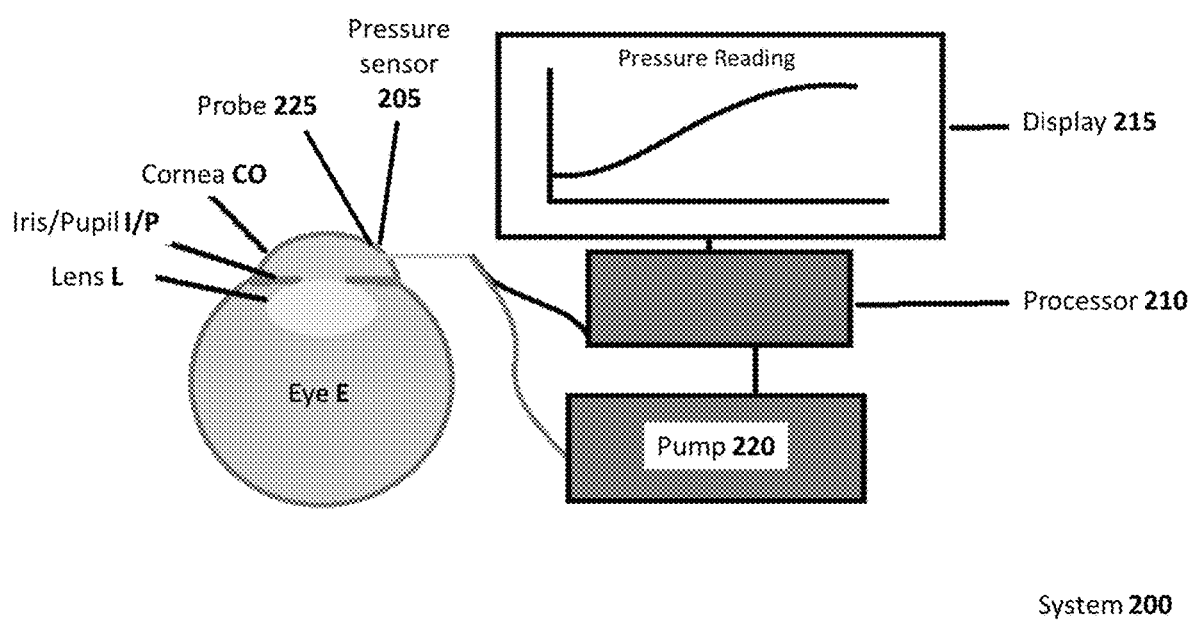
FIG. 2 illustrates an example intraocular pressure monitoring system of the invention in use with an eye.

FIG. 2 illustrates an example system 200 for monitoring dynamic fluid outflow from an eye E of a subject. The system 200 may include a pressure sensor 205 communicatively coupled to a processor 210, such as a computer processor. The pressure sensor 205 can be wirelessly or physically coupled to a processor 210. The processor 210 can receive pressure data, process the pressure data, and transmit the pressure data to a recording device of the processor 210 and a display 215. A pump 220 can be configured or programmed to infuse a volume of fluid into the eye E through a probe 225 via an infusion line. This probe 225 can be attached to a handpiece that contains the pressure sensor 205 and a catheter. The probe 225 connected to the infusion line is inserted into the eye E at the cornea CO. In some cases, the probe 225 is configured to be inserted into the eye E at the cornea CO, but not at other areas of the eye, e.g., the iris/pupil I/P or the lens L. The sensor 205 can detect intraocular pressure of the eye E continuously and in real-time to characterize the dynamic fluid outflow behavior of the eye E. Thus, the sensor 205 indirectly detects changes in volume of fluid exiting the eye (i.e., fluid outflow of the eye) due to changes in IOP. The pump 220 can be connected or disconnected from the system 200. In some cases, such as during fluid challenge testing, the pump 220 can modulate infusion of a fluid to the eye from a fluid source (not shown). The pump 220 may be communicatively coupled to a computer processor 210 (data recorder/transmitter). The processor 210 may be communicatively coupled to the sensor 205 such that the processor 210 can receive and transmit IOP data associated with fluid outflow behavior of the eye E detected by the sensor 205. The processor 210 may generate a representation of the fluid outflow behavior based on the received data associated with IOP of the eye, e.g., a graphical representation of the fluid outflow behavior. The representation of outflow behavior can be electronically displayed on the display 215 that is communicatively coupled to the processor 210.

A volume of fluid can be infused into the eye E through the infusion line by the pump 220. A volumetric fluid infusion can cause an increase in IOP. Accordingly, the display 215 can illustrate a detected increase in IOP over time.

Figure 3:
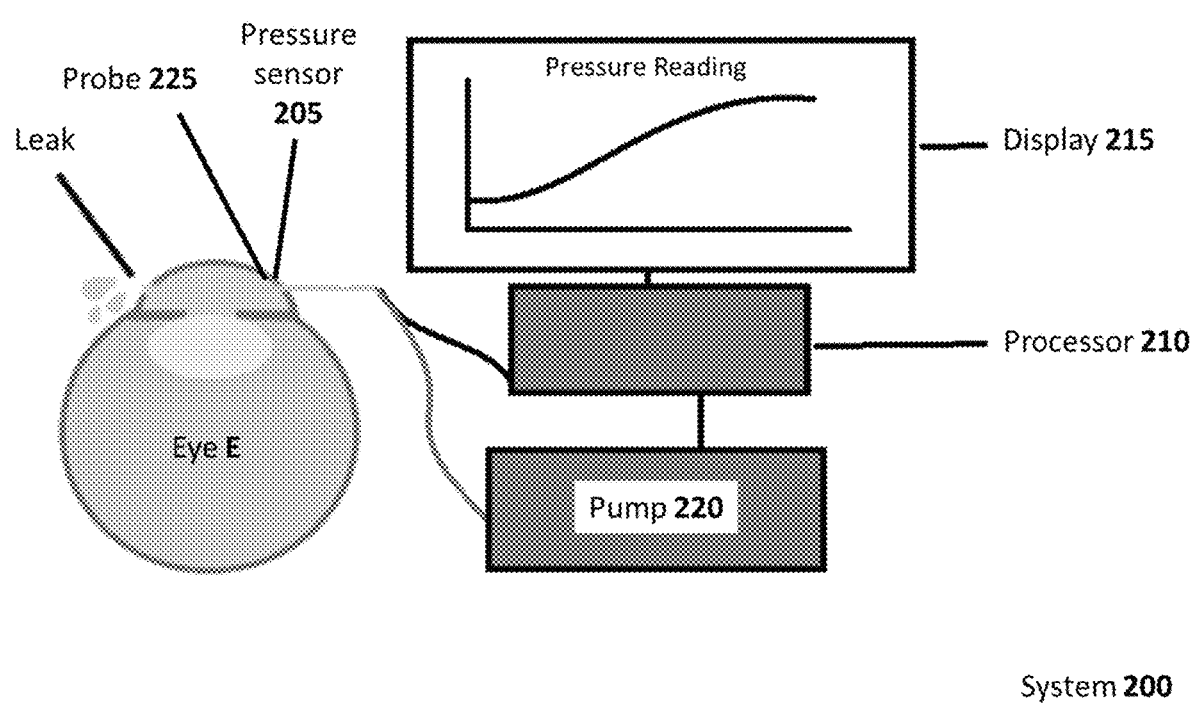
FIG. 3 illustrates an example intraocular pressure monitoring system of the invention in use with an eye with a fluid leak.

FIG. 3 illustrates the example system 200 of FIG. 2 when there is a leakage (leak) in the eye E. For example, the leakage can be due to fluid outflow from an incision in the eye, e.g., a surgical incision made during surgery. An increase in fluid outflow caused by the leakage can lead to reduction in IOP. The sensor 205 of the system 200 can illustrate in the display 215 a corresponding decrease in IOP in response to the infusion. Since fluid outflow behavior (and thus, IOP pressure) is displayed continuously and in real-time, a surgeon can immediately take an action during a procedure in response to an outflow behavior detected by the system.

At the beginning of or during an intraocular surgery, a micro-infusion/pressure sensor (MIPS) catheter can be inserted into the eye through the cornea or sclera. The system 200 can obtain a baseline biometric IOP measurement to characterize the initial dynamic fluid outflow state of a subject. Then, a micro-infusion "stress test" (i.e., a fluid challenge test) can be performed to assess the dynamic IOP response of the eye to the infusion. This assessment can be performed for about 10-20 minutes. During this time, the IOP can be measured continuously or intermittently as needed to generate a micro-interventional dynamic outflow curve (miDOC). Additional IOP measurements can be recorded to monitor changes in the miDOC throughout the course of the surgery.

Changes to the miDOC can guide the surgical intervention to achieve the optimal intraocular aqueous outflow dynamics, post-operative state, and post-operative outcomes. For example, during a trabeculectomy procedure, there can be leakage or high fluid outflow through the trabeculectomy flap (FIG. 3). Throughout the procedure, the system can detect corresponding IOP changes in the miDOC curve and process the changes in an electronic display (e.g., FIG. 4-9). Thus, the system can indicate whether a step of a surgical procedure is properly performed to reduce the likelihood of ocular damage due to abnormal fluid outflow behavior. If the fluid outflow behavior is stable, the miDOC trace may show a stable, consistent IOP values over time. If the fluid outflow is rising, then the miDOC trace may show decreasing IOP values over time. Based on the generated miDOC and clinical judgment, a surgeon can determine whether a corrective action may be needed.

Figure 4:
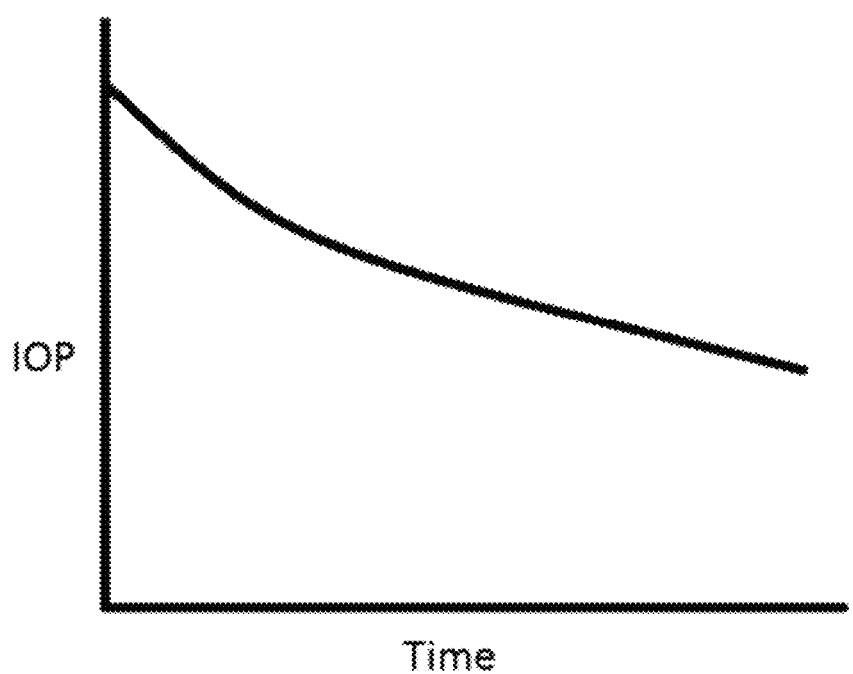
FIG. 4 illustrates an example fluid outflow curve corresponding to changes in IOP over time.

FIGS. 4-9 illustrates various example outflow curves corresponding to IOP changes during surgery. In FIG. 4, a pressure sensor is first introduced into a glaucomatous eye of a subject and the initial IOP (outflow behavior) is observed. In this example, the initial IOP is high and gradually decreases. However, the IOP remains high and does not decrease to zero.

Figure 5:
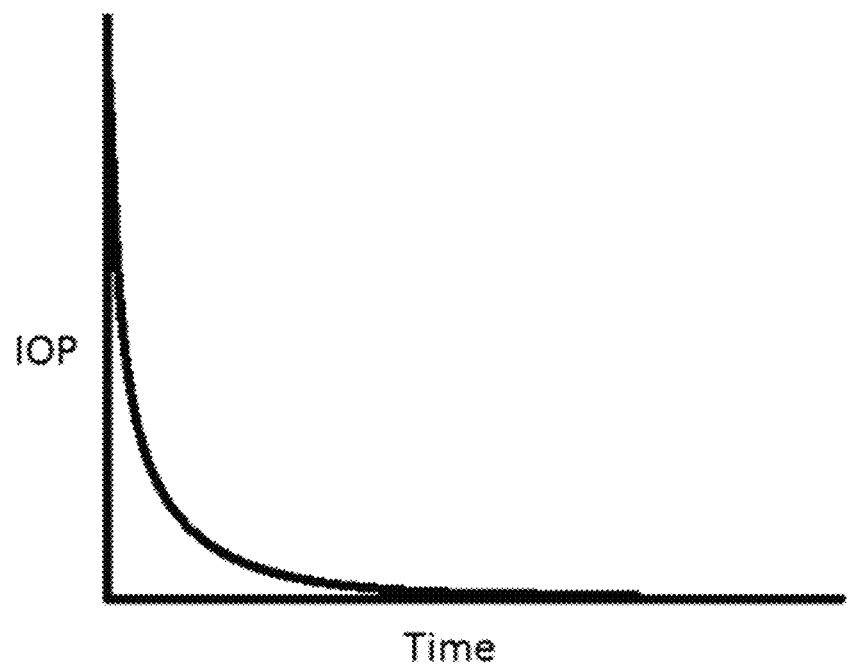
FIG. 5 illustrates an example fluid outflow curve corresponding to changes in IOP over time.
Figure 6:
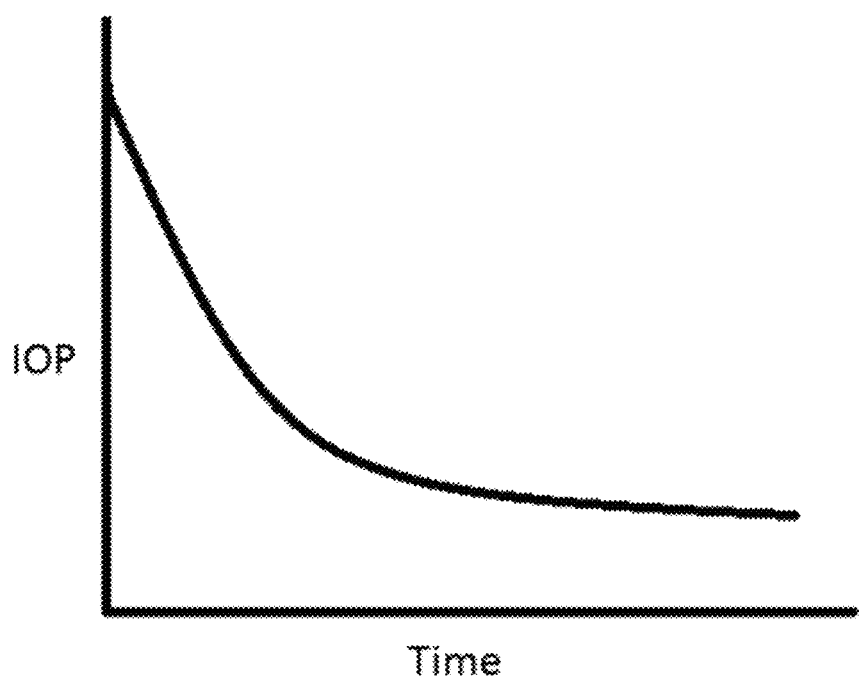
FIG. 6 illustrates an example fluid outflow curve corresponding to changes in IOP over time.

In FIG. 5, a surgeon performs a surgery on a patient to improve the fluid outflow facility by making an incision in the eye of the patient. However, because the incision is too large, the pressure drops rapidly to zero, suggesting that too much outflow occurred through the incision. This phenomenon can pose the patient at risk for hypotony, which can have dangerous post-operative consequences. Observing the data on the miDOC visual display of FIG. 5, the surgeon can quickly identify a problem, e.g., an incision is too large, and immediately adjust the size of the incision to mitigate the outflow rate. As shown in FIG. 6, adjusting the size of the incision improves the outflow behavior. The rate of IOP decreases faster than the rate of IOP measured pre-surgery as seen in FIG. 4, but the IOP does not drop as quickly and to a low pressure such that the patient is at risk for hypotony as seen in FIG. 5.

Figure 7:
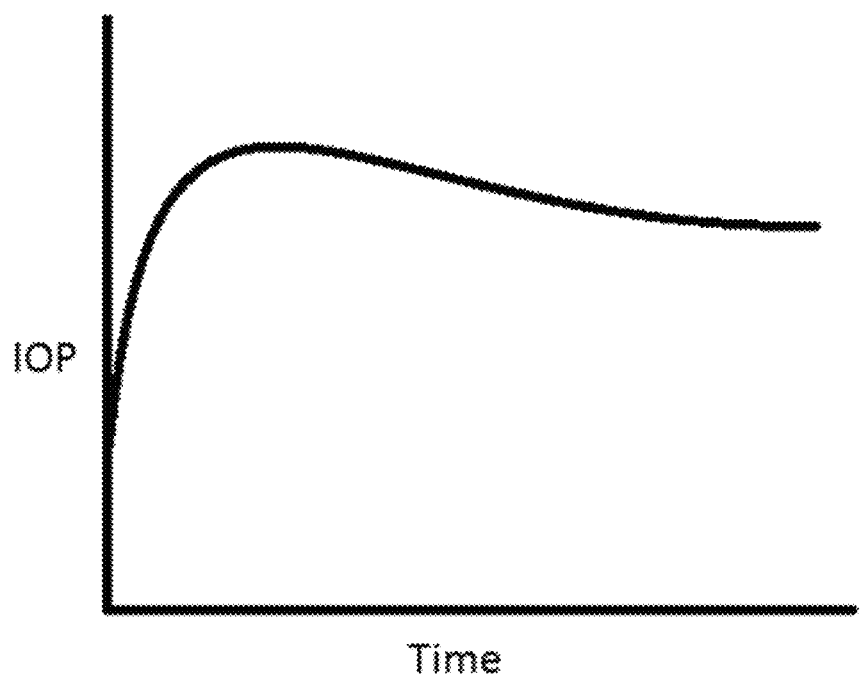
FIG. 7 illustrates an example fluid outflow curve corresponding to changes in IOP.
Figure 8:
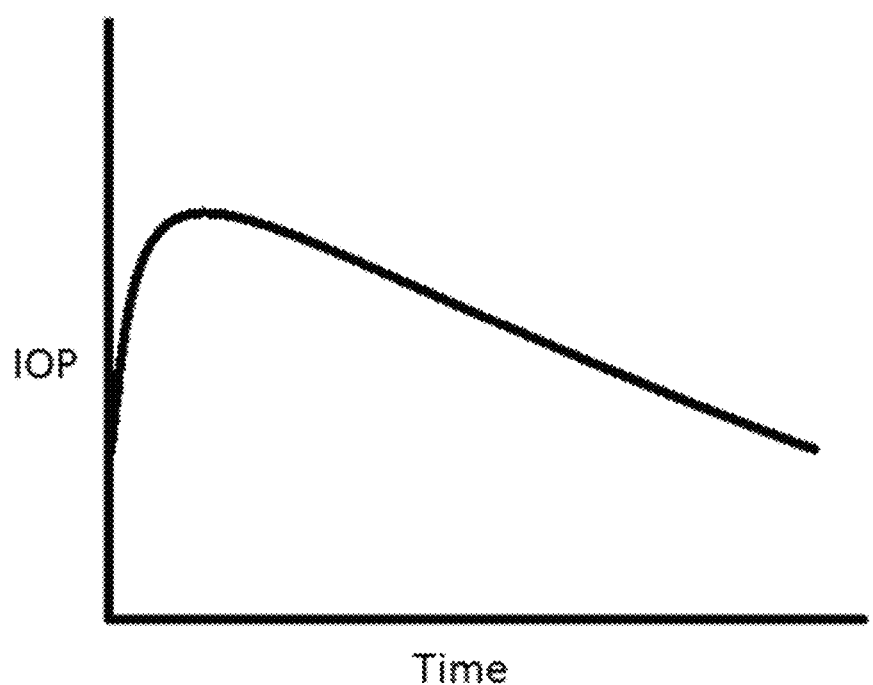
FIG. 8 illustrates an example fluid outflow curve corresponding to changes in IOP over time.

Optionally, the surgeon can perform a fluid challenge test to assess the eye's corresponding outflow behavior when challenged. Here, the surgeon can determine a volume of fluid or pressure value to infuse in the eye and inputs the desired amount into a computer processor that actuates and controls the pump. The computer processor can instruct the pump to infuse the desired volume of fluid into the eye. If a pressure value is inputted, the processor can determine an estimated volume of fluid that achieves the desired pressure value after infusion of the fluid. In a glaucomatous eye, the pressure can rise due to the infused fluid, but can remain elevated due to poor fluid outflow as shown in FIG. 7. The surgeon can then perform the glaucoma surgery and repeat the fluid challenge test, thereby verifying the improvement in the outflow facility of the eye. As illustrated in FIG. 8, the IOP increases due to the infusion, and then gradually decreases as a result of the surgery.

Figure 9:
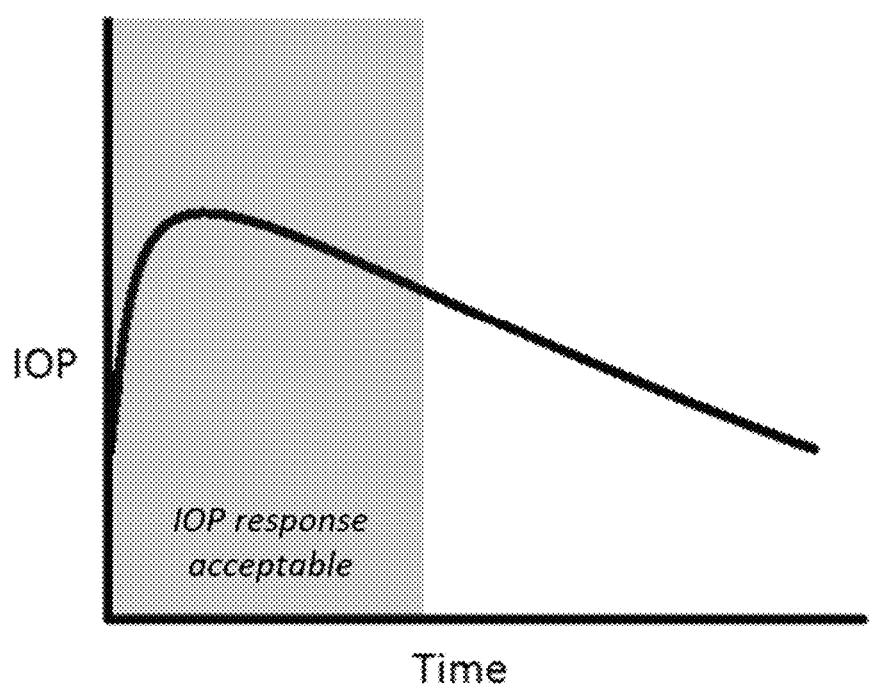
FIG. 9 illustrates an example fluid outflow curve corresponding to changes in IOP over time.

FIG. 9 illustrates an example guidance system for assisting a surgeon in determining whether an outflow behavior or pressure response, e.g., the pressure response shown in FIG. 8, is within a normal or desirable range. The guidance system provides a visual marker of a normal or desirable IOP range overlaid on the detected outflow (or IOP) behavior. During a glaucoma surgery, a surgeon can apply the fluid challenge test using the system to confirm that the IOP has improved within the acceptable IOP range before terminating a surgery.

Example 2. Monitoring Dynamic Fluid Outflow in an Ex-Vivo Porcine Eye

Ocular procedures were conducted on ex-vivo, enucleated, whole porcine eyes using a dynamic fluid outflow monitoring system described herein. The system comprised of an infusion line having a probe, a sensor configured to detect the intraocular pressure of the eye, and a processor configured to display a fluid outflow pattern based on the intraocular pressure of the eye. Each of the procedures confirmed compatibility with the fluid outflow monitoring system.

Infusion

An infusion experiment was conducted to assess the effects of fluid infusion on outflow behavior monitored using the system described herein. The needle probe of the infusion line was inserted into the eye. The pressure detected by the sensor was then monitored to verify that the IOP was stabilized to steady state outflow facility following insertion.

Fluid was then infused into the eye at a constant flow rate of 0.2 mL/2 sec via the infusion line. The resulting pressure detected by the sensor was again monitored to verify steady state outflow facility of the eye. The intraocular pressure detected by the sensor was processed and generated by processor to display the corresponding fluid outflow behavior. The initial infusion caused a rise in pressure, followed by a gradual pressure decay back to steady state.

Next, fluid was infused into the eye at a higher constant flow rate of 0.4 mL/4 sec via the infusion line. The resulting pressure detected by the sensor was again monitored to verify steady state outflow facility of the eye. Stabilization of the IOP following infusion indicated no leakages, e.g., through any incisions on the eye.

Outflow Mirroring

An outflow mirroring experiment was conducted to assess the effects of multiple incisions on outflow behavior monitored using the system described herein. In addition to the needle probe, a 30 G needle was inserted into the eye to avoid wound closing. IOP detected by the sensor was monitored until the dynamic IOP stabilized to steady state.

Fluid was then infused into the eye at a constant flow rate of 0.2 mL/2 sec via the infusion line. Again, IOP detected by the sensor was monitored until the IOP stabilized to steady state. The IOP was closely monitored to verify absence of any leaks in the eye that would contribute to a continuously decreasing IOP or low IOP.

Fluid was then infused into the eye at a constant flow rate of 0.4 mL/4 sec via the infusion line. Again, IOP detected by the sensor was monitored until the IOP stabilized to steady state. The IOP was closely monitored to verify absence of any leaks in the eye that would contribute to a decreasing IOP or low IOP.

A second 30 G needle was then inserted into the eye to avoid wound closing. Again, IOP detected by the sensor was monitored until the IOP stabilized to steady state. At this point, three needles are inserted into the eye with one needle connected to the miDOC device via the infusion line.

About 100 µL of fluid was infused into the eye. IOP detected by the sensor was monitored until the IOP stabilized to steady state and the absence of leaks was confirmed.

About 200 µL of fluid was infused into the eye. IOP detected by the sensor was monitored until the IOP stabilized to steady state and the absence of leaks was confirmed.

The two 30 G needles were then removed from the eye. IOP detected by the sensor was monitored until the IOP stabilized to steady state and the absence of leaks was confirmed.

Trabeculectomy and IOP

In a new, fresh porcine eye, a trabeculectomy surgical procedure was conducted to assess compatibility with the fluid outflow monitoring system described herein. The needle probe of the infusion line was insert into the eye. The pressure detected by the sensor was then monitored to verify that the IOP stabilized to steady state outflow facility following insertion.

Using surgical instruments, the traction suture was performed. IOP detected by the sensor was then monitored until the IOP stabilized to steady state.

Using surgical instruments, the conjunctival incision was performed. IOP detected by the sensor was then monitored until the IOP stabilized to steady state.

Using surgical instruments, the scleral flap shape and dissection was performed. IOP detected by the sensor was then monitored until the IOP stabilized to steady state.

Using surgical instruments, the peripheral iridectomy was performed. IOP detected by the sensor was then monitored until the IOP stabilized to steady state.

Using surgical instruments, the sutures were performed. Sutures were confirmed to be sufficiently tight. IOP detected by the sensor was then monitored until the IOP stabilized to steady state.

Fluid was then infused into the eye at a constant flow rate of 0.2 mL/2 sec via the infusion line. Again, IOP detected by the sensor was monitored until the IOP stabilized to steady state. The IOP was closely monitored to identify any non-accounted leaks in the eye that would contribute to a continuously decreasing IOP or low IOP.

Fluid was then infused into the eye at a constant flow rate of 0.4 mL/4 sec via the infusion line. Again, IOP detected by the sensor was monitored until the IOP stabilized to steady state. The IOP was closely monitored to identify any non-accounted leaks in the eye that would contribute to a continuously decreasing IOP or low IOP.

Using surgical instruments, the sutures were then loosened. The resulting outflow behavior was monitored to assess the corresponding effect.

Fluid was then infused into the eye at a constant flow rate of 0.2 mL/2 sec via the infusion line for a second time. IOP detected by the sensor was monitored until the IOP stabilized to steady state. The IOP was closely monitored to identify any non-accounted leaks in the eye that would contribute to a continuously decreasing IOP or low IOP.

Fluid was then infused into the eye at a constant flow rate of 0.4 mL/4 sec via the infusion line for a second time. IOP detected by the sensor was monitored until the IOP stabilized to steady state. The IOP was closely monitored to identify any non-accounted leaks in the eye that would contribute to a continuously decreasing IOP or low IOP.

Trabeculectomy and IOP—Simplified

In a new, fresh porcine eye, a simplified trabeculectomy surgical procedure was conducted to assess compatibility with the fluid outflow monitoring system described herein. The fluid outflow monitoring system described herein can assist in determining the success of the surgery based on the resulting fluid outflow behavior after each step of the procedure. The system can also guide the surgical procedure, e.g., by determining how tight to make the scleral flap or determining how tight to make the suture.

The needle probe of the infusion line was inserted into the eye. The pressure detected by the sensor was then monitored to verify that the IOP stabilized to steady state outflow facility following insertion.

Fluid was then infused into the eye at a constant flow rate of 0.2 mL/2 sec via the infusion line. IOP detected by the sensor was monitored until the IOP stabilized to steady state. The IOP was closely monitored to identify any non-accounted leaks in the eye that would contribute to a continuously decreasing IOP or low IOP.

Using surgical instruments, a scleral flap was created in the eye. IOP detected by the sensor was monitored until the IOP stabilized to steady state.

Using surgical instruments, a paracentesis was created in the anterior chamber of the eye through the base of the scleral bed under the scleral flap. IOP detected by the sensor was monitored until the IOP stabilized to steady state.

Using surgical instruments, sutures were placed and tightened to close the flap. IOP detected by the sensor was monitored until the IOP stabilized to steady state.

Fluid was then infused into the eye at a constant flow rate of 0.2 mL/2 sec via the infusion line a second time. IOP detected by the sensor was monitored until the IOP stabilized to steady state. The IOP was closely monitored to identify any non-accounted leaks in the eye that would contribute to a continuously decreasing IOP or low IOP.

Using surgical instruments, the sutures were then loosened. IOP detected by the sensor was monitored until the IOP stabilized to steady state.

Goniotomy Testing

The goniotomy procedure using a Kahook Dual Blade device is a microinvasive glaucoma surgical procedure for reducing IOP. Using a special mirrored lens, a Kahook Dual blade is used to create parallel incisions in the trabecular meshwork and open up the inner wall of Schlemm's canal to improve aqueous humor outflow from the eye, thereby reducing eye pressure. Meshwork removal is dictated in clock hours or degrees.

In a new, fresh porcine eye, a goniotomy procedure was conducted to assess compatibility with the fluid outflow monitoring system described herein. The needle probe of the infusion line was inserted into the eye. The pressure detected by the sensor was then monitored to verify that the IOP stabilized to steady state outflow facility following insertion.

Fluid was then infused into the eye at a constant flow rate of 0.2 mL/2 sec via the infusion line. IOP detected by the sensor was monitored until the IOP stabilized to steady state. The IOP was closely monitored to identify any non-accounted leaks in the eye that would contribute to a continuously decreasing IOP or low IOP.

Using the Kahook Dual blade, a three-clock hour incision was performed. IOP detected by the sensor was monitored until the IOP stabilized to steady state.

Fluid was again infused into the eye at a constant flow rate of 0.2 mL/2 sec via the infusion line. IOP detected by the sensor was monitored until the IOP stabilized to steady state. The IOP was closely monitored to identify any non-accounted leaks in the eye that would contribute to a continuously decreasing IOP or low IOP.

Using the Kahook Dual blade, a six-clock hour incision was performed. IOP detected by the sensor was monitored until the IOP stabilized to steady state.

Fluid was again infused into the eye at a constant flow rate of 0.2 mL/2 sec via the infusion line. IOP detected by the sensor was monitored until the IOP stabilized to steady state. The IOP was closely monitored to identify any non-accounted leaks in the eye that would contribute to a continuously decreasing IOP or low IOP.

Using the Kahook Dual blade, a nine-clock hour incision was performed. IOP detected by the sensor was monitored until the IOP stabilized to steady state.

Fluid was again infused into the eye at a constant flow rate of 0.2 mL/2 sec via the infusion line. IOP detected by the sensor was monitored until the IOP stabilized to steady state. The IOP was closely monitored to identify any non-accounted leaks in the eye that would contribute to a continuously decreasing IOP or low IOP.

Using the Kahook Dual blade, a twelve-clock hour incision was performed (all meshwork is removed). IOP detected by the sensor was monitored until the IOP stabilized to steady state.

Fluid was again infused into the eye at a constant flow rate of 0.2 mL/2 sec via the infusion line. IOP detected by the sensor was monitored until the IOP stabilized to steady state. The IOP was closely monitored to identify any non-accounted leaks in the eye that would contribute to a continuously decreasing IOP or low IOP.

Cataract Incision

In a new, fresh porcine eye, a cataract incision procedure was conducted to assess compatibility with the fluid outflow monitoring system described herein. The needle probe of the infusion line was inserted into the eye. The pressure detected by the sensor was then monitored to verify that the IOP stabilized to steady state outflow facility following insertion.

Fluid was then infused into the eye at a constant flow rate of 0.2 mL/2 sec via the infusion line. IOP detected by the sensor was monitored until the IOP stabilized to steady state. The IOP was closely monitored to identify any non-accounted leaks in the eye that would contribute to a continuously decreasing IOP or low IOP.

Paracentesis was then performed on the eye. IOP detected by the sensor was monitored until the IOP stabilized to steady state.

Fluid was then infused into the eye at a constant flow rate of 0.2 mL/2 sec via the infusion line. IOP detected by the sensor was monitored until the IOP stabilized to steady state. The IOP was closely monitored to identify any non-accounted leaks in the eye that would contribute to a continuously decreasing IOP or low IOP.

Fluid was then infused into the eye at a constant flow rate of 0.4 mL/4 sec via the infusion line. IOP detected by the sensor was monitored until the IOP stabilized to steady state. The IOP was closely monitored to identify any non-accounted leaks in the eye that would contribute to a continuously decreasing IOP or low IOP.

The main cataract incision was then performed. IOP detected by the sensor was monitored until the IOP stabilized to steady state.

Fluid was then infused into the eye at a constant flow rate of 0.2 mL/2 sec via the infusion line. IOP detected by the sensor was monitored until the IOP stabilized to steady state. The IOP was closely monitored to identify any non-accounted leaks in the eye that would contribute to a continuously decreasing IOP or low IOP.

Fluid was then infused into the eye at a constant flow rate of 0.4 mL/4 sec via the infusion line. IOP detected by the sensor was monitored until the IOP stabilized to steady state. The IOP was closely monitored to identify any non-accounted leaks in the eye that would contribute to a continuously decreasing IOP or low IOP.

Viscoelastic material was then injected into the eye to maintain the structure of the anterior chamber. IOP detected by the sensor was monitored until the IOP stabilized to steady state.

Fluid was then infused into the eye at a constant flow rate of 0.2 mL/2 sec via the infusion line. IOP detected by the sensor was monitored until the IOP stabilized to steady state. The IOP was closely monitored to identify any non-accounted leaks in the eye that would contribute to a continuously decreasing IOP or low IOP.

Fluid was then infused into the eye at a constant flow rate of 0.4 mL/4 sec via the infusion line. IOP detected by the sensor was monitored until the IOP stabilized to steady state. The IOP was closely monitored to identify any non-accounted leaks in the eye that would contribute to a continuously decreasing IOP or low IOP.

Viscoelastic material was then removed from the eye. IOP detected by the sensor was monitored until the IOP stabilized to steady state.

Fluid was then infused into the eye at a constant flow rate of 0.2 mL/2 sec via the infusion line. IOP detected by the sensor was monitored until the IOP stabilized to steady state. The IOP was closely monitored to identify any non-accounted leaks in the eye that would contribute to a continuously decreasing IOP or low IOP.

Fluid was then infused into the eye at a constant flow rate of 0.4 mL/4 sec via the infusion line. IOP detected by the sensor was monitored until the IOP stabilized to steady state. The IOP was closely monitored to identify any non-accounted leaks in the eye that would contribute to a continuously decreasing IOP or low IOP.

Embodiments

Embodiment A1. A system for monitoring a fluid outflow behavior of an eye of a subject, comprising: an infusion line configured to be inserted into the eye of the subject; a sensor configured to continuously detect an intraocular pressure of the eye of the subject over a time period; and a processor configured to generate a representation of the fluid outflow behavior the eye of the subject based on the intraocular pressure of the eye detected by the sensor.

Embodiment A2. The system of embodiment A1, wherein the sensor is configured to detect the intraocular pressure of the eye of the subject in real-time.

Embodiment A3. The system of embodiment A1 or A2, wherein the processor is configured to generate the representation of the fluid outflow behavior of the eye of the subject concurrently with the detecting of the intraocular pressure of the eye of the subject by the sensor.

Embodiment A4. The system of any one of embodiments A1-A3, further comprising a display, wherein the display is configured to electronically display the representation of the fluid outflow behavior of the eye of the subject.

Embodiment A5. The system of any one of embodiments A1-A4, further comprising a pump configured to infuse a replacement fluid to the eye of the subject.

Embodiment A6. The system of any one of embodiments A1-A5, wherein the time period is a duration of a surgical procedure being performed on the subject.

Embodiment A7. A method of modulating a fluid outflow behavior of an eye of a subject, comprising: inserting an infusion line into the eye of the subject; detecting continuously an intraocular pressure of the eye of the subject over a time period; monitoring the fluid outflow behavior of the eye of the subject based on the intraocular pressure of the eye detected by the sensor over the time period; and performing an intervention on the eye of the subject based on the fluid outflow behavior of the eye.

Embodiment A8. The method of embodiment A7, wherein a change in an intraocular pressure of the eye over the time period corresponds to the fluid outflow behavior of the eye of the subject.

Embodiment A9. The method of embodiment A7 or A8, wherein the inserting of the infusion line into the eye of the subject is through a probe.

Embodiment A10. The method of any one of embodiments A7-A9, wherein the detecting of the intraocular pressure of the eye of the subject is in real-time.

Embodiment A11. The method of any one of embodiments A7-A10, wherein the detecting of the intraocular pressure of the eye of the subject is while the subject is undergoing a surgery.

Embodiment A12. The method of any one of embodiments A7-A11, wherein the intervention modulates the fluid outflow behavior of the eye of the subject.

Embodiment A13. The method of any one of embodiments A7-A12, further comprising modifying the intervention based on the fluid outflow behavior of the eye of the subject.

Embodiment A14. The method of any one of embodiments A7-A13, further comprising infusing a volume of a replacement fluid into the eye of the subject through the infusion line.

Embodiment A15. A method of monitoring a fluid outflow behavior of an eye of a subject, comprising: detecting continuously an intraocular pressure of the eye of the subject over a time period; and generating a representation of the fluid outflow behavior of the eye of the subject based on the intraocular pressure of the eye detected by the sensor over the time period.

Embodiment A16. The method of embodiment A15, wherein a change in an intraocular pressure of the eye over the time period corresponds to the fluid outflow behavior of the eye of the subject.

Embodiment A17. The method of embodiment A15 or A16, wherein the detecting of the intraocular pressure of the eye of the subject is in real-time.

Embodiment A18. The method of any one of embodiments A15-A17, wherein the detecting of the intraocular pressure of the eye of the subject is while the subject is undergoing a surgery.

Embodiment A19. The method of any one of embodiments A15-A18, further comprising infusing a volume of a replacement fluid into the eye of the subject through the infusion line.

Embodiment A20. The method of any one of embodiments A15-A19, wherein the generating of the representation of the fluid outflow behavior is concurrent with the detecting of the intraocular pressure of the eye of the subject.

Embodiment B1. A system for monitoring a fluid outflow behavior of a tissue compartment of a subject, comprising: an infusion line configured to be inserted into the tissue compartment of the subject; a sensor configured to detect a pressure within the tissue compartment over a time period; and a processor configured to generate a representation of the fluid outflow behavior of the tissue compartment based on the pressure within the tissue compartment detected by the sensor over the time period.

Embodiment B2. The system of embodiment B1, wherein the sensor is configured to continuously detect the pressure within the tissue compartment of the subject.

Embodiment B3. The system of embodiment B1 or B2, wherein the sensor is configured to detect the pressure within the tissue compartment of the subject in real-time.

Embodiment B4. The system of any one of embodiments B1-B3, wherein the processor is configured to generate the representation of the fluid outflow behavior of the tissue compartment of the subject concurrently with the detecting of the pressure within the tissue compartment of the subject by the sensor.

Embodiment B5. The system of any one of embodiment B1-B4, wherein the processor is configured to generate the representation of the fluid outflow behavior of the tissue compartment of the subject in real-time.

Embodiment B6. The system of any one of embodiments B1-B5, further comprising a display, wherein the display is configured to electronically display the representation of the fluid outflow behavior of the tissue compartment of the subject.

Embodiment B7. A system for monitoring a fluid outflow behavior of an eye of a subject, comprising: an infusion line configured to be inserted into the eye of the subject; a sensor configured to detect an intraocular pressure of the eye of the subject over a time period; and a processor configured to generate a representation of the fluid outflow behavior of the eye of the subject based on the intraocular pressure of the eye detected by the sensor over the time period.

Embodiment B8. The system of embodiment B7, wherein a change in an intraocular pressure of the eye over the time period corresponds to the fluid outflow behavior of the eye of the subject.

Embodiment B9. The system of embodiment B7 or B8, wherein the infusion line comprises the sensor.

Embodiment B10. The system of any one of embodiments B7-B9, wherein the sensor is configured to continuously detect the intraocular pressure of the eye of the subject.

Embodiment B11. The system of any one of embodiments B7-B10, wherein the sensor is configured to detect the intraocular pressure of the eye of the subject in real-time.

Embodiment B12. The system of any one of embodiments B7-B11, wherein the processor is configured to receive data associated with the fluid outflow behavior of the eye of the subject.

Embodiment B13. The system of any one of embodiments B7-B10, wherein the processor is communicatively coupled to the to the sensor.

Embodiment B14. The system of any one of embodiments B7-B13, wherein the processor is configured to generate the representation of the fluid outflow behavior of the eye of the subject concurrently with the detecting of the intraocular pressure of the eye of the subject by the sensor.

Embodiment B15. The system of any one of embodiments B7-B14, wherein the processor is configured to continuously generate the representation of the fluid outflow behavior of the eye of the subject.

Embodiment B16. The system of any one of embodiments B7-B15, wherein the processor is configured to generate the representation of the intraocular pressure of the eye of the subject in real-time.

Embodiment B17. The system of any one of embodiments B7-B16, further comprising a display, wherein the display is configured to electronically display the representation of the fluid outflow behavior of the eye of the subject.

Embodiment B18. The system of embodiment B17, wherein the display is communicatively coupled to the processor.

Embodiment B19. The system of any one of embodiments B7-B18, further comprising a pump configured to infuse a replacement fluid to the eye of the subject.

Embodiment B20. The system of embodiment B19, wherein the replacement fluid is a saline solution or a pH balanced solution.

Embodiment B21. The system of any one of embodiments B7-B20, further comprising a probe configured to be inserted into the eye of the subject.

Embodiment B22. The system of any one of embodiments B7-B21, wherein the infusion line is configured to be inserted into the eye of the subject through the probe.

Embodiment B23. The system of any one of embodiments B7-B22, wherein the time period is a duration of a surgical procedure being performed on the subject.

Embodiment B24. A method of modulating a fluid outflow behavior of an eye of a subject, comprising: inserting an infusion line into the eye of the subject; detecting an intraocular pressure of the eye of the subject over a time period; and performing an intervention on the eye of the subject based on the intraocular pressure of the eye of the subject.

Embodiment B25. The method of embodiment B24, wherein a change in an intraocular pressure of the eye over the time period corresponds to the fluid outflow behavior of the eye of the subject.

Embodiment B26. The method of embodiment B24 or B25, wherein the inserting of the infusion line into the eye of the subject is through a probe.

Embodiment B27. The method of any one of embodiments B24-B26, wherein the detecting of the intraocular pressure of the eye of the subject is continuous.

Embodiment B28. The method of any one of embodiments B24-B27, wherein the detecting of the intraocular pressure of the eye of the subject is in real-time.

Embodiment B29. The method of any one of embodiments B24-B28, wherein the detecting of the intraocular pressure of the eye of the subject is while the subject is undergoing a surgery.

Embodiment B30. The method of any one of embodiments B24-B29, wherein the intervention is a surgical procedure, modification of a procedure, abortion of a procedure, or a pharmaceutical intervention.

Embodiment B31. The method of any one of embodiments B24-B30, wherein the intervention modulates the fluid outflow behavior of the eye of the subject.

Embodiment B32. The method of any one of embodiments B24-B31, wherein the intervention modulates an intraocular pressure of the subject.

Embodiment B33. The method of any one of embodiments B24-B32, further comprising modifying the intervention based on the fluid outflow behavior of the eye of the subject.

Embodiment B34. The method of any one of embodiments B24-B33, further comprising analyzing an electronical display of the representation of the fluid outflow behavior of the eye of the subject.

Embodiment B35. The method of any one of embodiments B24-B34, further comprising inferring a prognosis of the subject based on the fluid outflow behavior of the eye of the subject.

Embodiment B36. The method of any one of embodiments B24-B35, further comprising infusing a volume of a replacement fluid into the eye of the subject through the infusion line.

Embodiment B37. The method of embodiment B36, wherein the replacement fluid is a saline solution or a pH balanced solution.

Embodiment B24. A method of modulating a fluid outflow behavior of an eye of a subject, comprising: inserting an infusion line into the eye of the subject; detecting an intraocular pressure of the eye of the subject over a time period; and performing an intervention on the eye of the subject based on the intraocular pressure of the eye of the subject.

Embodiment B25. The method of embodiment B24, wherein a change in an intraocular pressure of the eye over the time period corresponds to the fluid outflow behavior of the eye of the subject.

Embodiment B26. The method of embodiment B24 or B25, wherein the inserting of the infusion line into the eye of the subject is through a probe.

Embodiment B27. The method of any one of embodiments B24-B26, wherein the detecting of the intraocular pressure of the eye of the subject is continuous.

Embodiment B28. The method of any one of embodiments B24-B27, wherein the detecting of the intraocular pressure of the eye of the subject is in real-time.

Embodiment B29. The method of any one of embodiments B24-B28, wherein the detecting of the intraocular pressure of the eye of the subject is while the subject is undergoing a surgery.

Embodiment B30. The method of any one of embodiments B24-B29, wherein the intervention is a surgical procedure, modification of a procedure, abortion of a procedure, or a pharmaceutical intervention.

Embodiment B31. The method of any one of embodiments B24-B30, wherein the intervention modulates the fluid outflow behavior of the eye of the subject.

Embodiment B32. The method of any one of embodiments B24-B31, wherein the intervention modulates an intraocular pressure of the subject.

Embodiment B33. The method of any one of embodiments B24-B32, further comprising modifying the intervention based on the fluid outflow behavior of the eye of the subject.

Embodiment B34. The method of any one of embodiments B24-B33, further comprising analyzing an electronical display of the representation of the fluid outflow behavior of the eye of the subject.

Embodiment B35. The method of any one of embodiments B24-B34, further comprising inferring a prognosis of the subject based on the fluid outflow behavior of the eye of the subject.

Embodiment B36. The method of any one of embodiments B24-B35, further comprising infusing a volume of a replacement fluid into the eye of the subject through the infusion line.

Embodiment B37. The method of embodiment B36, wherein the replacement fluid is a saline solution or a pH balanced solution.

Embodiment B38. A method of monitoring a fluid outflow behavior of an eye of a subject, comprising: detecting an intraocular pressure of the eye of the subject over a time period; and generating a representation of the fluid outflow behavior of the eye of the subject based on the intraocular pressure of the eye detected by the sensor over the time period.

Embodiment B39. The method of embodiment B38, wherein a change in an intraocular pressure of the eye over the time period corresponds to the fluid outflow behavior of the eye of the subject.

Embodiment B40. The method of any one of embodiments B38-B39, wherein the detecting of the intraocular pressure of the eye of the subject is in real-time.

Embodiment B41. The method of any one of embodiments B38-B40, wherein the detecting of the intraocular pressure of the eye of the subject is while the subject is undergoing a surgery.

Embodiment B42. The method of any one of embodiments B38-B41, further comprising infusing a volume of a replacement fluid into the eye of the subject through the infusion line.

Embodiment B43. The method of embodiment B42, wherein the replacement fluid is a saline solution or a pH balanced solution.

Embodiment B44. The method of any one of embodiments B38-B43, wherein the generating of the representation of the fluid outflow behavior of the eye of the subject is by a processor.

Embodiment B45. The method of any one of embodiments B38-B44, wherein the generating of the representation of the fluid outflow behavior of the eye of the subject is continuous.

Embodiment B46. The method of any one of embodiments B38-B45, wherein the generating of the representation of the fluid outflow behavior of the eye of the subject is in real-time.

Embodiment B47. The method of any one of embodiments B38-B46, wherein the generating of the representation of the fluid outflow behavior of the eye of the subject is concurrent with the detecting of the intraocular pressure of the eye of the subject.

Embodiment B48. The method of any one of embodiments B38-B47, further comprising receiving data associated with the fluid outflow behavior of the eye of the subject.

Embodiment B49. The method of any one of embodiments B38-B48, further comprising transmitting data associated with the fluid outflow behavior of the eye of the subject.

Embodiment B50. The method of any one of embodiments B38-B49, further comprising electronically displaying the representation of the fluid outflow behavior of the eye of the subject.

Embodiment B51. The method of any one of embodiments B38-B50, further comprising recommending an intervention for the subject based on the fluid outflow behavior of the eye of the subject.

Embodiment B52. The method of any one of embodiments B38-B51, further comprising performing an intervention on the subject based on the fluid outflow behavior of the eye of the subject.

Embodiment B53. The method of any one of embodiments B38-B52, wherein the intervention modulates the fluid outflow behavior of the eye.

Embodiment B54. The method of any one of embodiments B38-B53, further comprising modifying a surgical procedure to be performed on the subject based on the fluid outflow behavior of the eye of the subject.

Embodiment B55. The method of any one of embodiments B38-B54, further comprising determining a prognosis of the subject based on the fluid outflow behavior of the eye of the subject.

What is claimed is:

1. A system for monitoring a fluid outflow facility of an eye of a subject, comprising:
    an infusion line configured to be inserted into the eye of the subject to deliver a volume of fluid into the eye;
    a sensor communicatively coupled to the infusion line, wherein the sensor is configured to continuously detect fluid outflow of the eye over a time period in response to the delivered volume of fluid; and
    a processor communicatively coupled to the infusion line and the sensor, wherein the processor is configured to:
        generate a representation of the detected fluid outflow of the eye over the time period, wherein the representation is indicative of a behavior pattern of the fluid outflow of the eye, and
        provide, based on the representation, an indication of whether the behavior pattern is normal or abnormal.

2. The system of claim 1, wherein the infusion line is configured to be inserted into the eye through a probe, wherein the probe comprises a sealed entry port, wherein the sealed entry port prevents leakage of fluid from where the infusion line is inserted into the eye.

3. The system of claim 2, wherein the sensor is communicatively coupled to the infusion line at the probe.

4. The system of claim 2, wherein the sensor is communicatively coupled to the infusion line remotely from the probe.

5. The system of claim 1, wherein the sensor is configured to continuously detect the fluid outflow of the eye in real-time.

6. The system of claim 1, wherein the sensor is configured to continuously detect the fluid outflow of the eye in vivo.

7. The system of claim 1, wherein the processor is configured to generate the representation of the detected fluid outflow of the eye that is indicative of the behavior pattern of the fluid outflow of the eye concurrently with the detecting of the fluid outflow of the eye by the sensor.

8. The system of claim 1, further comprising a pump communicatively coupled to the infusion line, wherein the pump is configured to infuse a replacement fluid into the eye of the subject through the infusion line, and wherein the representation of the detected fluid outflow of the eye is further based on a change to intraocular pressure of the eye in response to an infusion of the replacement fluid into the eye.

9. The system of claim 1, wherein the representation is one or more of visual, audio, and tactile.

10. The system of claim 1, wherein the processor is configured to provide, based on the behavior pattern of the fluid outflow of the eye, a recommended surgical intervention, and wherein the surgical intervention is selected to increase the fluid outflow of the eye if the behavior pattern is indicated as abnormal and the behavior pattern shows a rise in intraocular pressure of the eye in response to the delivered volume of fluid and the intraocular pressure remaining elevated longer than normal.

11. The system of claim 1, wherein the processor is configured to provide, based on the behavior pattern of the fluid outflow of the eye, a recommended surgical intervention, and wherein the surgical intervention is selected to decrease the fluid outflow of the eye if the behavior pattern is indicated as abnormal and the behavior pattern shows a rise in intraocular pressure of the eye in response to the delivered volume of fluid and the intraocular pressure rapidly decreasing faster than normal.

12. The system of claim 1, wherein the surgical intervention is a glaucoma surgical procedure.

13. The system of claim 1, wherein the behavior pattern of the fluid outflow of the eye includes fluid outflow from an artificial leakage in the eye.

14. The method of claim 1, wherein the sensor is configured to continuously detect intraocular pressure of the eye.

15. A method comprising:
infusing, through an infusion line, a volume of fluid into an eye of a subject;
continuously detecting the volume of the fluid injected into the eye over a time period; and
generating a representation of fluid outflow facility of the eye based on the continuously detected volume of fluid injected into the eye over the time period.

16. The method of claim 15, wherein the infusion of the volume of fluid through the infusion line into the eye is through a probe.

17. The method of claim 15, wherein the continuous detecting of the volume of fluid infused into the eye is in real-time.

18. The method of claim 15, wherein the continuously detecting of the volume of the fluid infused into the eye is in vivo.

19. The method of claim 15, wherein the continuously detecting of the volume of the fluid infused into the eye of the subject is while the subject is undergoing a medical procedure.

20. The method of claim 15, further comprising performing a surgical intervention on the eye of the subject to modulate post-operative fluid outflow facility of the eye, and wherein the surgical intervention is selected based on the generated representation of the fluid outflow of the eye to modulate the fluid outflow facility of the eye of the subject.

21. The method of claim 15, further comprising modifying the intervention on the eye based on the generated representation of the fluid outflow of the eye.

22. The method of claim 20, wherein the surgical intervention is selected to increase fluid outflow of the eye if the generated representation of the fluid outflow of the eye shows a rise in intraocular pressure of the eye in response to the delivered volume of fluid and the intraocular pressure remaining elevated longer than normal.

23. The method of claim 20, wherein the surgical intervention is selected to decrease fluid outflow of the eye if the generated representation of the fluid outflow of the eye shows a rise in intraocular pressure of the eye in response to the delivered volume of fluid and the intraocular pressure rapidly decreasing faster than normal.

24. The method of claim 20, wherein the surgical intervention is a glaucoma surgical procedure.

25. The method of claim 15, wherein the time period is a duration of a medical procedure being performed on the eye of the subject.

26. The method of claim 15, wherein the time period is at least 0.2 seconds.

27. The method of claim 15, wherein the volume of fluid infused into the eye is detected by a sensor that is in fluid communication with the infusion line.

28. The method of claim 15, wherein the representation of the fluid outflow facility includes fluid outflow from an artificial leakage in the eye.

29. A method of monitoring a fluid outflow facility of an eye of a subject, comprising:
continuously detecting, by a sensor, a fluid outflow of the eye of the subject over a time period in response to an infusion of a volume of fluid into the eye of the subject;
generating a representation of the detected fluid outflow of the eye, wherein the representation is indicative of a behavior pattern of the fluid outflow of the eye; and
providing, based on the representation, an indication of whether the behavior pattern is normal or abnormal.

30. The method of claim 29, wherein the detecting of the fluid outflow facility of the eye is in real-time.

31. The method of claim 29, wherein the detecting of the fluid outflow facility of the eye is in vivo.

32. The method of claim 29, wherein the detecting of the fluid outflow facility of the eye of the subject is while the subject is undergoing a medical procedure.

33. The method of claim 29, wherein the generating of the representation of the detected fluid outflow of the eye is concurrent with the detecting of the fluid outflow of the eye.

34. The method of claim 29, wherein the representation is one or more of visual, audio, and tactile.

35. The method of claim 29, further comprising infusing the volume of fluid into the eye through an infusion line.

36. The method of claim 35, further comprising, after infusing the replacement fluid into the eye, continuously detecting the intraocular pressure of the eye over a later time period.

37. The method of claim 29, further comprising providing a recommendation to perform or modify a surgical intervention on the eye based on the indication of whether the behavior pattern is normal or abnormal, and wherein the surgical intervention is selected to increase the fluid outflow of the eye if the behavior pattern is indicated as abnormal and the behavior pattern shows a rise in intraocular pressure of the eye in response to the delivered volume of fluid and the intraocular pressure remaining elevated longer than normal.

38. The method of claim 29, further comprising providing a recommendation to perform or modify a surgical intervention on the eye based on the indication of whether the behavior pattern is normal or abnormal, and wherein the surgical intervention is selected to decrease fluid outflow of the eye if the behavior pattern is indicated as abnormal and the behavior pattern shows a rise in intraocular pressure of the eye in response to the delivered volume of fluid and the intraocular pressure rapidly decreasing faster than normal.

39. The method of claim 29, further comprising providing a recommendation to perform or modify a surgical intervention on the eye based on the indication of whether the behavior pattern is normal or abnormal, and wherein the surgical intervention is a glaucoma surgical procedure.

40. The method of claim 29, wherein the behavior pattern of the fluid outflow of the eye includes fluid outflow from an artificial leakage in the eye.

* * * * *